(12) United States Patent
Simonsen

(10) Patent No.: US 7,850,972 B2
(45) Date of Patent: Dec. 14, 2010

(54) CRYPTOSPORIDIUM PARVUM ANTIGENS, ANTIBODIES THERETO AND DIAGNOSTIC AND THERAPEUTIC COMPOSITIONS THEREOF

(75) Inventor: J. Neil Simonsen, Winnipeg (CA)

(73) Assignee: University of Manitoba, Winnipeg (CA)

( * ) Notice: Subject to any disclaimer, the term of this patent is extended or adjusted under 35 U.S.C. 154(b) by 48 days.

(21) Appl. No.: 11/900,817

(22) Filed: Sep. 13, 2007

(65) Prior Publication Data

US 2008/0299143 A1     Dec. 4, 2008

Related U.S. Application Data

(60) Division of application No. 10/948,490, filed on Sep. 23, 2004, now Pat. No. 7,288,621, which is a continuation of application No. 09/881,556, filed on Jun. 14, 2001, now Pat. No. 6,808,900.

(60) Provisional application No. 60/212,083, filed on Jun. 15, 2000.

(51) Int. Cl.
 A61K 39/00     (2006.01)
 C07K 14/00     (2006.01)
(52) U.S. Cl. .................. 424/185.1; 424/191.1; 530/350
(58) Field of Classification Search .................. None
See application file for complete search history.

(56) References Cited

U.S. PATENT DOCUMENTS

| 5,591,434 A | 1/1997 | Jenkins et al. |
| 5,643,772 A | 7/1997 | Petersen et al. |
| 5,773,245 A | 6/1998 | Wittrup et al. |
| 6,323,020 B1 | 11/2001 | Perryman et al. |

FOREIGN PATENT DOCUMENTS

WO     WO 98/07320 A     2/1998

OTHER PUBLICATIONS

Arrowood et al., "Effect of Immune Colostrum and Orally Adminstered Antisporozoite Monoclonal Antibodies on the Outcome of Cryptosporidium parvum Infections in neonatal Mice," Infect. Immun. 57(8):2283-2288 (1989).
Bjorneby et al., "Monoclonal Antibodiy Immunotherapy in Nude Mice Persistently Infected with Cryptosporidium parvum," Infect. Immun. 59(3):1172-1176 (1993).
Campbell et al., "Demonstration of Serum Antibodies to Cryptospridium sp. In Normal and Immunodeficient Humans with Confirmed Infections," Journal of Clinical Microbiology 18(1):165-169 (1983).
Doyle et al., "Anti-Cryptosporidium parvum Antibodies Inhibit Infectivity In Vitro and In Vivo," Infect. Immun. 61:4079-4084 (1993).

Jenkins et al., "Cloning and Expression of a cDNA Encoding Epitopes Shared by 15-and 60-Kilodalton Proteins of Cryptosporidium parvum Sporozoites," Infection and Immunity 61(6):2377-2382 (1993).
Jenkins et al., "Cloning and Expression of cDanA Encoding an Antigenic Cryptosporidium parvum Protein," Molecular and Biochemical Parasitology 71:149-152 (1995).
Lillehoj et al., "CD8$^+$T Cell-Coccidia Interactions," Parsitology Today 10:10-16 (1994).
McDonald et al., "Localization of Parsite Antigens in Cryptosporidium parvum-Infected Epithelial Cells Using Monoclonal Antibodies," Parasitology 110:259-268 (1995).
Mead, J.R. et al., "Antigens of Cryptosporidium Sporozoites Recognized by Immune Sera of Infected Animals and Humans," Journal of Parasitology 74(1):135-143 (1988).
Nina et al., "Analysis of Oocyst Wall and Sporozoite Antigens from Three Cryptosporidium Species," Infection and Immunity 60(4):1509-1513 (1992).
Nord et al., "Treatment of AID Associated Cryptosporidiosis With Hyperimmune Colostrum From Cows Vaccinated with Cryptosporidium," Fifth International Conference on Aids, Montreal, Quebec, May 1989.
Ortega-Mora et al., "Cross-Reactivity of Polyclonal Serum Antibodies Generated Against Cryptosporidium parvum Oocyst," Infection and Immunity 60(8):3442-3445 (1992).
Peeters et al., "Cryptosporidium parvum in Calves: Kinetics and Immunoblot Analysis of Specific Serum and Local Antibody Responses (Immunoglobulin A [IgA], IgG, and IgM) After Natural and Experimental Infections," Infection and Immunity 60(6):2309-2316 (1992).
Peterson et al., "Identification and Initial characterization of Five Cryptosporidium parvum Sporozoite Antigen Genes," Infection and Immunity 60(6):2343-2348 (1992).
Ranucci et al., "Characterization and Immunolocalization of a Cryptosporidium Protein Containing Repeated Amino Acid Motifs," Infection and Immunity 61(6):2347-2356 (1993).
Reperant, Jean-Michel et al., "Major Antigens of Cryptosporidium parvum Recognized by Serum Antibodies from Different Infected Animal Species and Man," Veterinary Parasitology 55(1-2):1-13 (1994).
Strong, W.B. et al., "Cloning and Sequence Analysis of a Highly Polymorphic Cryptosporidium parvum Gene Encoding a 60-Kilodalton Glycoprotein and Characterization of its 15-and 45-Kilodalton Ziote Surface Antigen Products," Infection and Immunity, American Society For Microbiology, Washington, U.S. 68(7):4117-4134 (2000).
Tzipori et al., "Remission of Diarhoea due to cryptosporidiosis in an Immunodeficient Child Treated with Hyperimmune Bove Colostrum," British Medical Journal 293:1276-1277 (1986).

(Continued)

Primary Examiner—Mark Navarro
(74) Attorney, Agent, or Firm—Robins & Pasternak LLP

(57) ABSTRACT

Cloning and expression of genes encoding C. parvum antigenic polypeptides are described as are antibodies that recognize epitopes on these polypeptides. The antigenic polypeptides and antibodies thereto can be used in therapeutic compositions for the prevention and treatment of C. parvum infections, as well as in diagnostic methods for determining the presence of C. parvum infections.

15 Claims, 9 Drawing Sheets

OTHER PUBLICATIONS

Ungar et al., "Cessation of *Cryptosporidium*-Associated Diarrehea in an Acquired Immunodeficiency Syndrome Patient After Treatment With Hyperimmune Bovine Colostrum," *Gastroenterology* 98:486-489 (1990).

Whitmire et al., "Characterization of Bovine Cellular and Serum Antibody Responses during Infection by *Cryptosporidium parvum*," *Infection and Immunity* 59(3):990-995 (1991).

Accession No. AF178459 "Neutralising Antigen 2 of *Cryptosporidium parvum* Recognised by Human Immune Sera," XP002205089, Sep. 5, 2000.

Accession No. AF178460 "Neutralising Antigen 1 of *C. parvum* Recognised by Human Immune Sera," XP0021694444, Sep. 5, 2000.

Accession No. AQ411949 "CpG 0925 A C[OPWAgDMA1 *C. parvum* Genomics, Genomic Survey Sequence," XP002205088, Mar. 25, 1999.

Accession No. AQ988925 "*Cryptosporidium parvum* Genomic Clone 25A1A08NE," XP002194443, Feb. 3, 2000.

Riggs et al., "Neutralization-Sensitive Epitopes Are Exposed on the Surface of Infectious *Cryptosporidium parvum* Sporozoites," *The Journal of Immunolology* 1989 143(4):1340-1345.

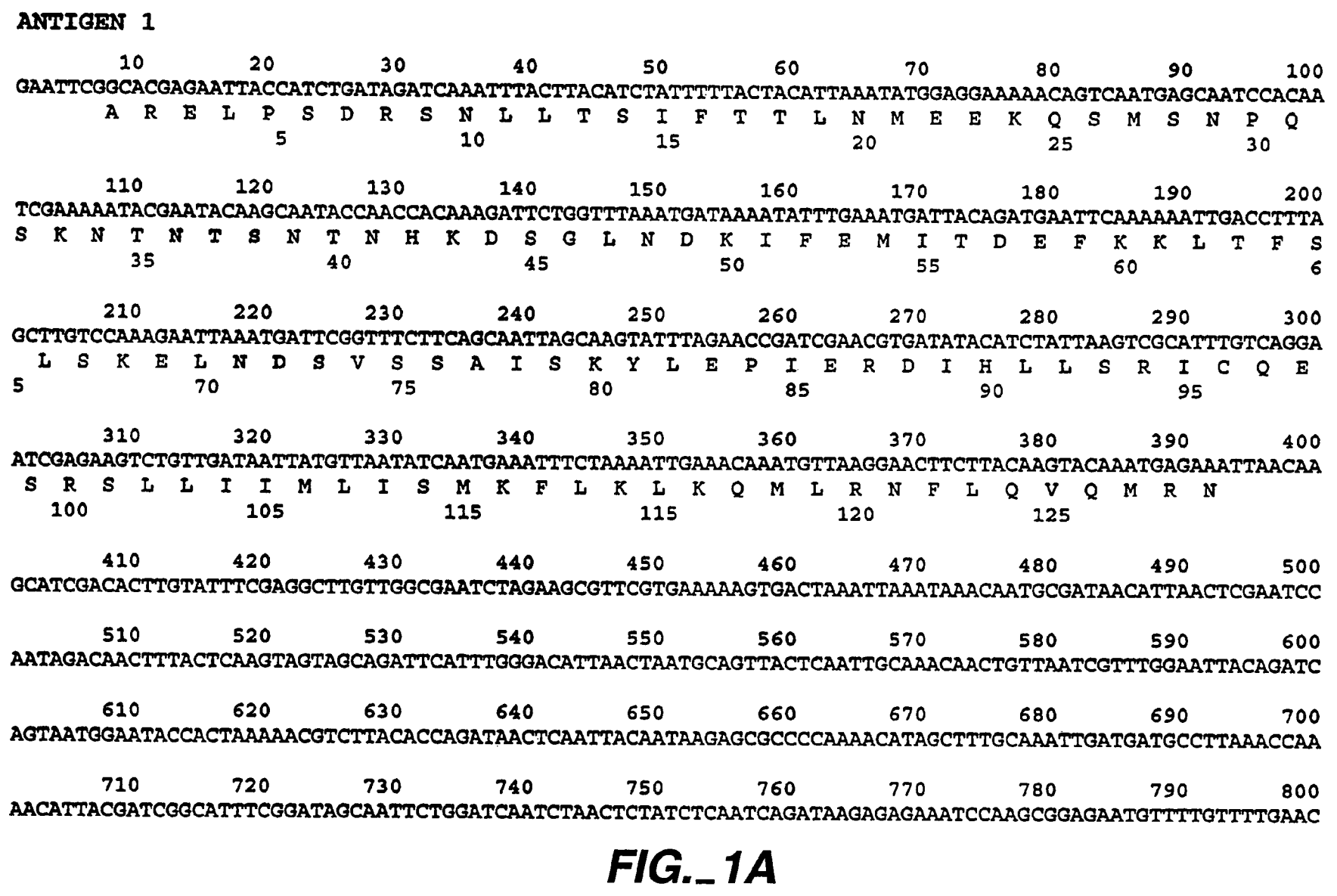

ANTIGEN 1

FIG._1A

```
    810       820       830       840       850       860       870       880       890       900
CTTGCATATAAGTTTGACCCATGTGTTTGGTTGGATGATCCAGCTTCCTATTAGCCATCCAGTAATATTAGGAATTCAAAAATTTGAGCGATACTCTT 910       920       930       940       950       960       970       980       990      1000
CCTCATTTAATTGAATCTTTAAAGACCAGCTGTAATTTTTCTCAAATTAGCTGCATTTCAGATTTAAAATTGAGAATTATGGATAAAAGAAACCATTC 1010      1020      1030      1040      1050      1060      1070      1080      1090      1100
ACTGTTTGAACCATTACTGATACTCTTACACCTAGTAGTGAGTAATGCAAATACTAAATTTCAGAAGTATGAACAAATGCATTAGCATTATAAATT 1110      1120      1130      1140      1150      1160      1170      1180      1190      1200
CGGTTAGCGATGCAAGTAAAAGCATGAACTATATTGTACCTGCATGCTTCACGGATGGGTCGATCATCAGTGATATTACTAGCATATTAAGGCATATTAG 1210      1220      1230      1240      1250      1260      1270      1280      1290      1300
AAGGACAACTAGAAAATATTACATCTGGAATTAGAATTAAGGGGTAGAATTAGAATATTTTTCATGTAAATTAGCGTTATTGAGGATTATTC 1310      1320      1330      1340      1350      1360      1370      1380
GAAATAAATAATAGAGATATTAAGTTTAGTTTTTATTTAAAAAAAAAAAAAAAAAAAAAAAAAAAAAACTCGAG
```

*FIG._1B*

ANTIGEN 2

```
         10         20         30         40         50         60         70         80         90        100
GAATTCGGCACGAGAGATTTTTTTTTTCTTTTTACCTATTTCAATTAGTTTCTTTGATTCAAACGATGCAAAGTCATTATTGTTTAAATCCAGATGGATC
  H  E  I  F  F  L  L  P  I  S  I  S  F  F  D  S  N  D  A  K  S  L  F  V  L  N  P  D  G  S
                 5                 10                 15                 20                 25                 30

110        120        130        140        150        160        170        180        190        200
CGGAATTTGAAAACACATTTGAAATTAAATTTGAGCTTGGCTTGATAAATGGTAGTTGGCTCGGAGGTGATATTTTTATCCTTGATAGG
  G  I  L  K  N  I  S  T  K  F  E  I  K  F  E  L  G  L  I  N  G  S  W  L  G  G  D  I  F  I  L  D  R
          35                 40                 45                 50                 55                 60

210        220        230        240        250        260        270        280        290        300
AAACACGCTCTTGAAGCTGTAAGTTATTCAATGCTGTGTTTCTATACAAAAACACTGTTTGAAAAGAATGAAGCACATTGTCTTAAACCCTTTAATC
  K  H  A  L  E  A  V  S  Y  S  I  A  C  V  F  Y  T  K  T  C  F  E  K  N  E  A  H  C  L  K  P  F  N  R
 65                 70                 75                 80                 85                 90                 95

310        320        330        340        350        360        370        380        390        400
GCGCTGAGAATAAAATGACTTTTGGTTCTGAGAAAGACTTAGCAACAACTCTCCAATCTCTAATTCTTCAATCTTCCTTACATGGAATAACTG
  A  E  N  K  M  T  F  G  S  E  K  D  L  A  T  T  L  Q  S  S  N  S  E  Y  Y  L  F  L  T  W  N  N  C
         100                115                                         120                125                130

410        420        430        440        450        460        470        480        490        500
CATTCTTGGATATATTCCAATTAACACAAATAAAATCAACAAAATTTCTCTTGAAAGTTCCGGAGAAAACTCAATTCCACAATTGGATATATTGGAGTATT
  I  L  G  Y  I  P  I  N  T  N  K  I  N  K  I  N  K  I  S  L  E  S  S  G  E  N  S  I  S  T  I  G  Y  W  S  I
         135                140                145                150                155                160

510        520        530        540        550        560        570        580        590        600
ATCGATGGATTTTCTTCTCTTAATTAAACAAGCCCTATAAAGAATCAAAATATTCAAGAATAATCAAATATTCAAATTCAAAATGAAATAATGAAG
  I  D  G  F  S  S  L  I  K  H  A  P  I  K  E  N  G  H  L  N  N  Q  E  S  K  Y  S  K
 65                170                175                180                185                190
```

FIG._2A

```
      610        620        630        640        650        660        670        680        690        700
CCACTAAACTTCAACAAATCAGGTGGGAATAACTTAAACTCAGAACCAAAACACAAAGCCTCATCCAGTTGTTAGACCGCATCCTACAGAAAAGC 710        720        730        740        750        760        770        780        790        800
CCTCAAATGGTGAACACATCAAGAATCTGGTTCAGAGCAAGCCCCTATTACCTCACCAGAGAAAACGAATCAAGTTCAAATCATCCTTCTGTGACAGTTCCAGA 810        820        830        840        850        860        870        880        890        900
TACTGGATCAGTTCAAATCTCCCTTCGTTACTATTCCAGAGACTGGATCAGATCAGAGACTCAGATCACGCGCCTTGTGACAATTCCAGAGACTGGATCAGTTCAAA 910        920        930        940        950        960        970        980        990       1000
TCATCTTCTGCTACTATACCAGAAACAGGATCCAGTCAGATCACACACTCTGCTACTTCTCCAGAAGAAGGATTGGACTCAGAACGTTACCAATCACTTCT 1010       1020       1030       1040       1050       1060       1070       1080       1090       1100
ACAGAACAAACTCAAAGCCAGTACATATCCTAACCAAGAAAATCATAATAATGAAAATCATCAGGAAGGTAATTCGAGTTTTAATACACTAAAATCTTCCAAA 1110       1120       1130       1140       1150       1160       1170       1180       1190       1200
TCAACCCAATCTTTCACGCAAGCTGGCAGATGTGGAAAGTTATGGGGAAAAGGATAATCACTAAAAATGACATTATT 1210       1220       1230       1240       1250       1260       1270       1280       1290       1300
GAAGATACTTCGAAAGAAATTAGAAACAAAAATGTAAAGTATCTCGCATTGATAAATATGGCCTTAGCCATTTCCAAATATCTAAATTGTCAACTCAAGTAA 1310       1320
AAAAAAAAAAAAAAAACTCGAG
```

FIG._2B

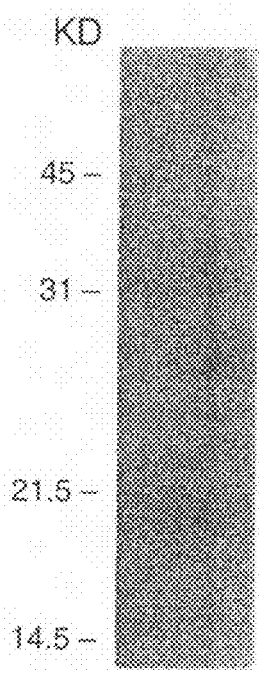
FIG._3A
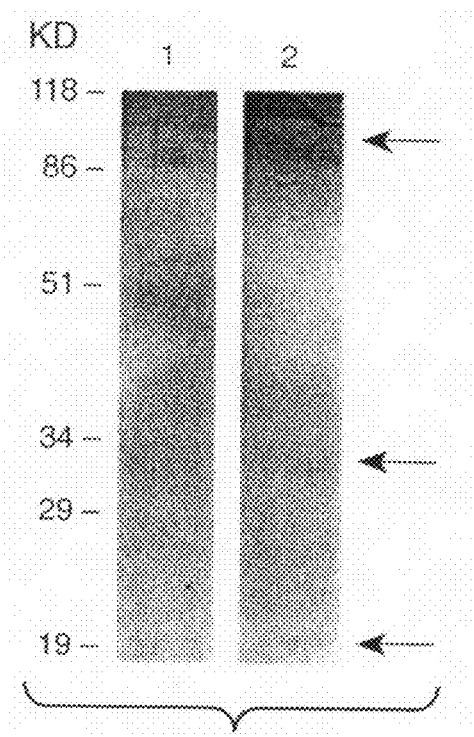
FIG._3B
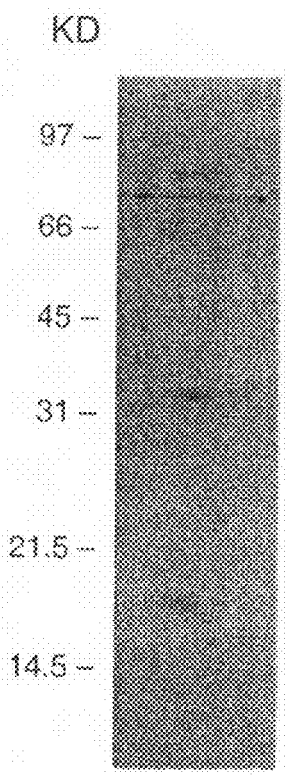
FIG._4A
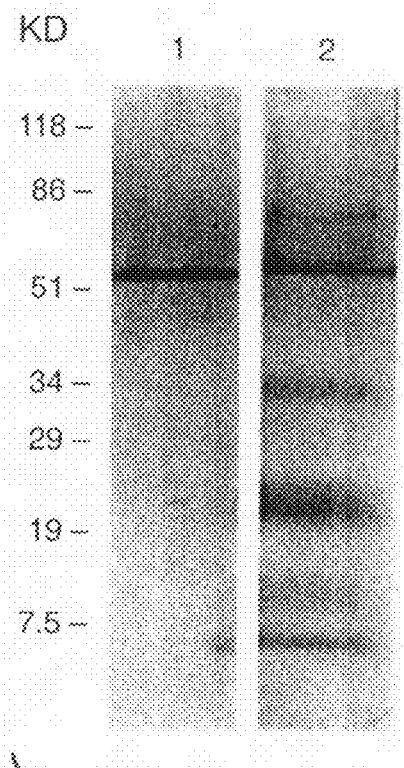
FIG._4B

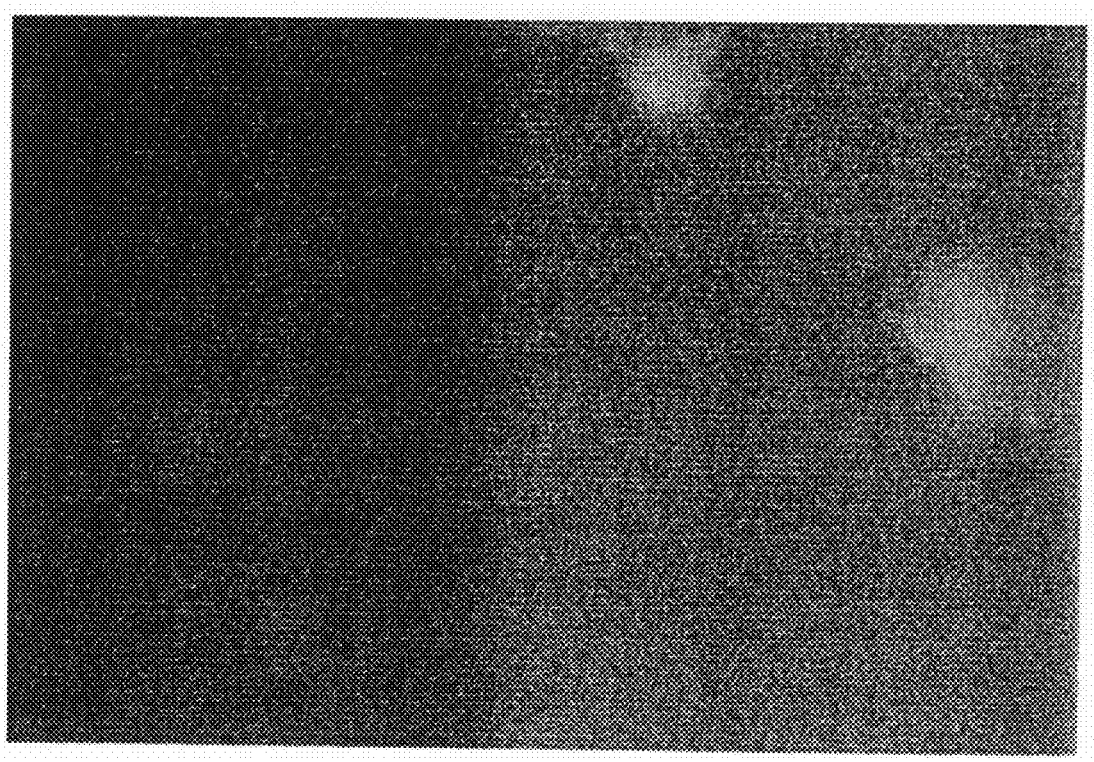
*FIG._5A*
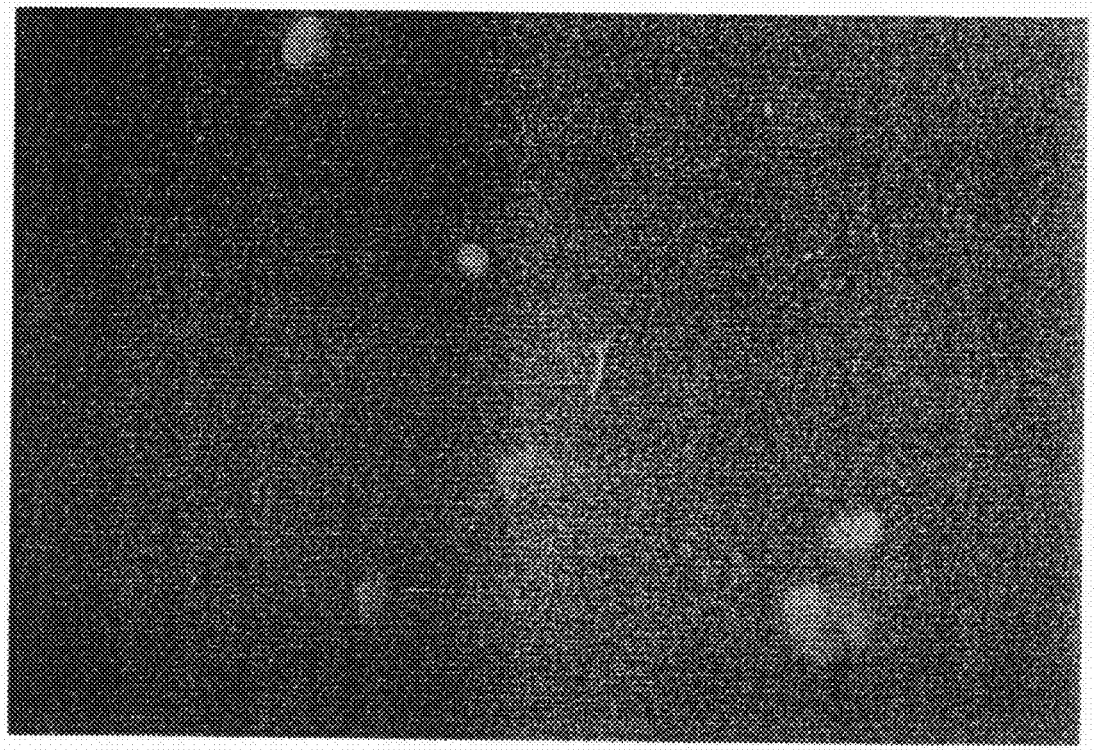
*FIG._5B*

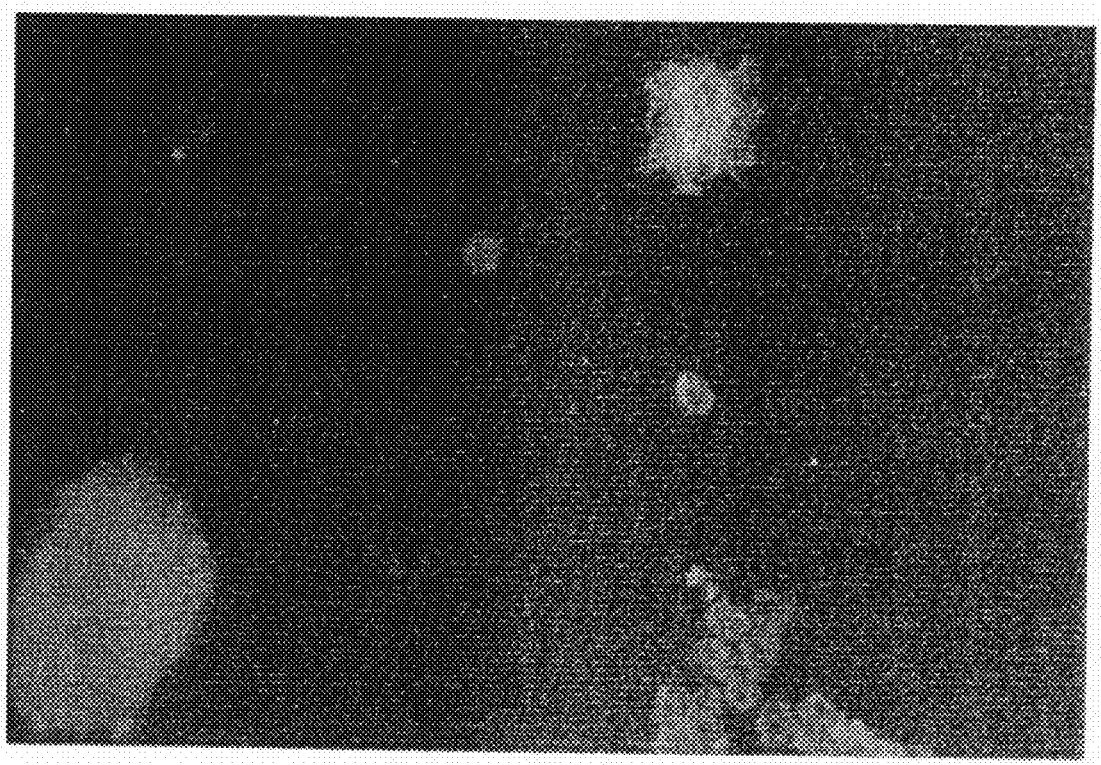
FIG._5C
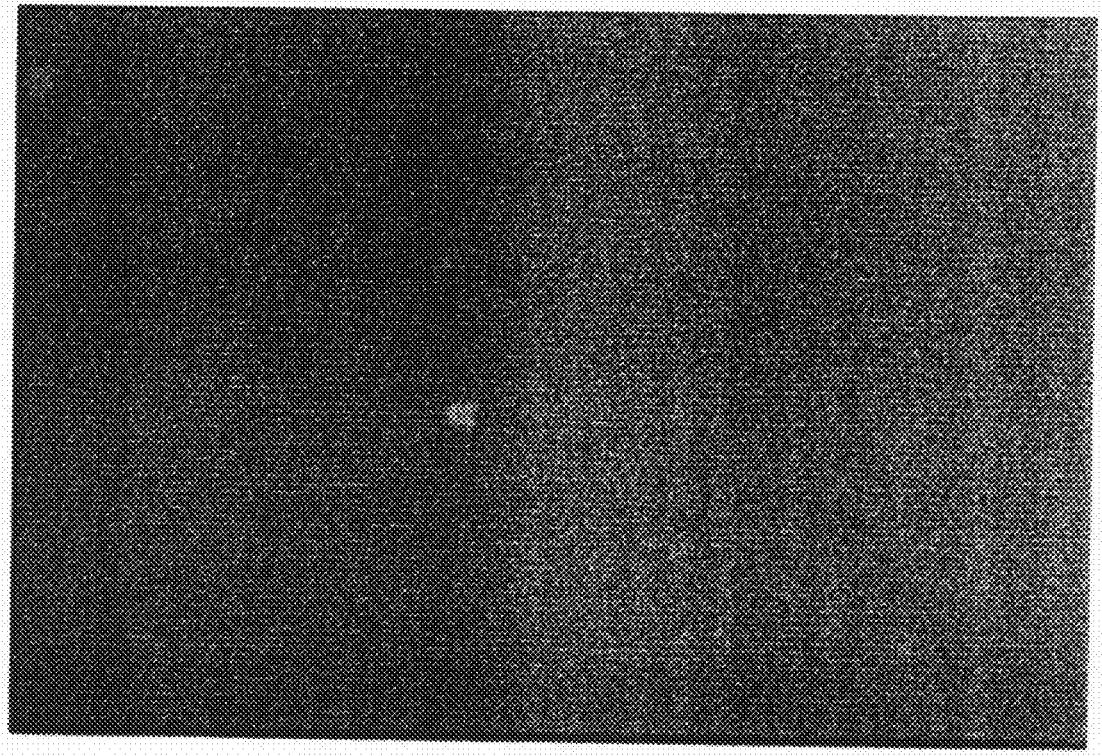
FIG._5D

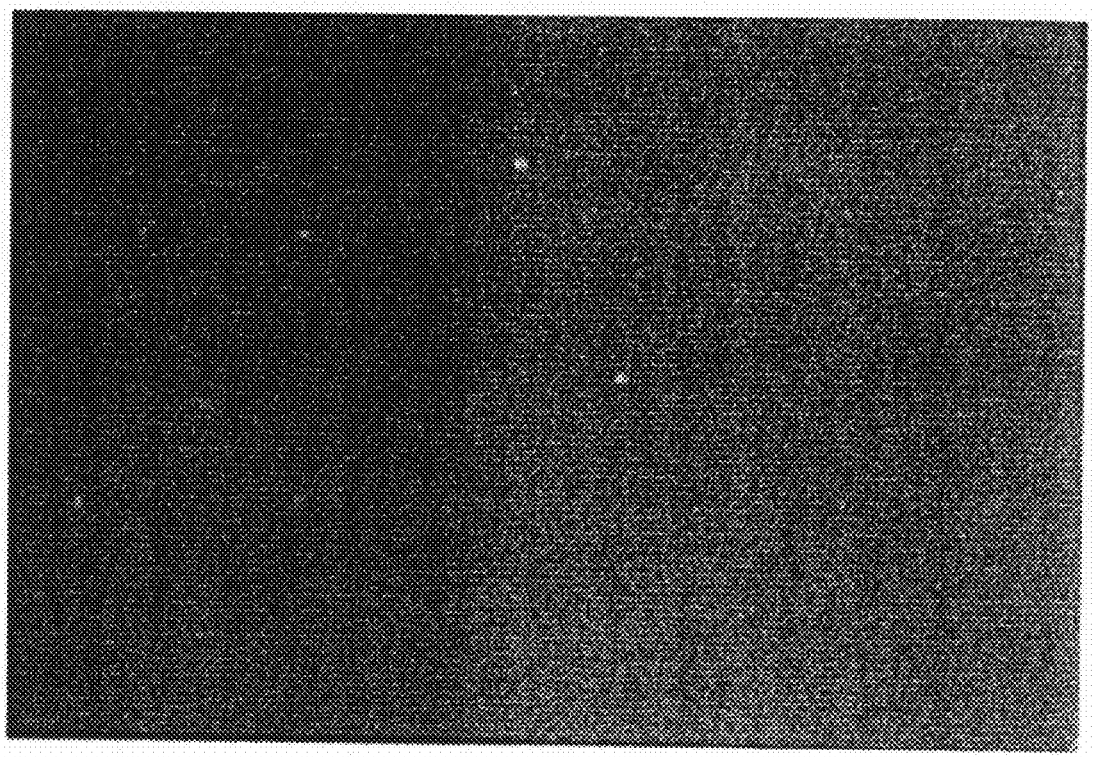
FIG._5E
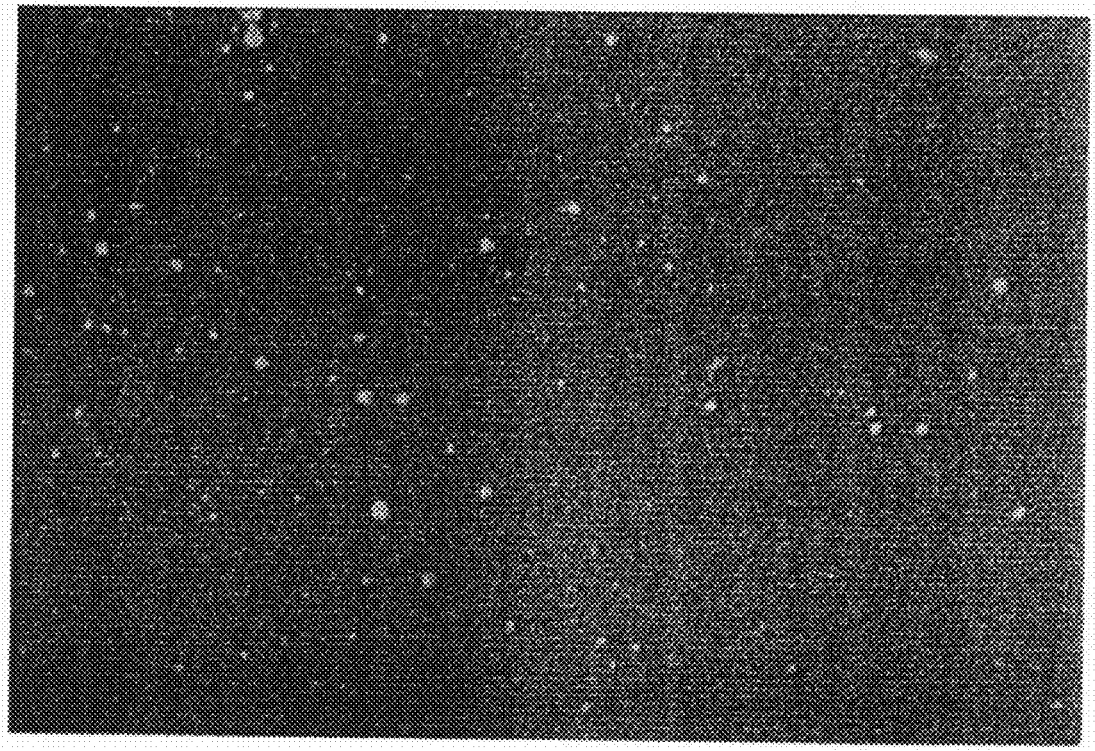
FIG._5F

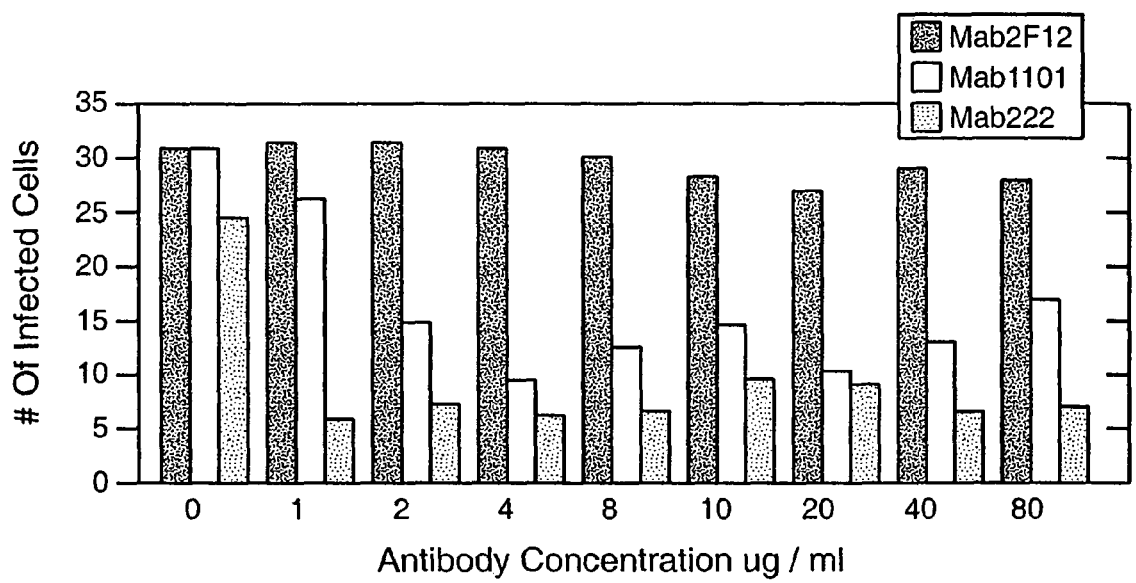
FIG._6
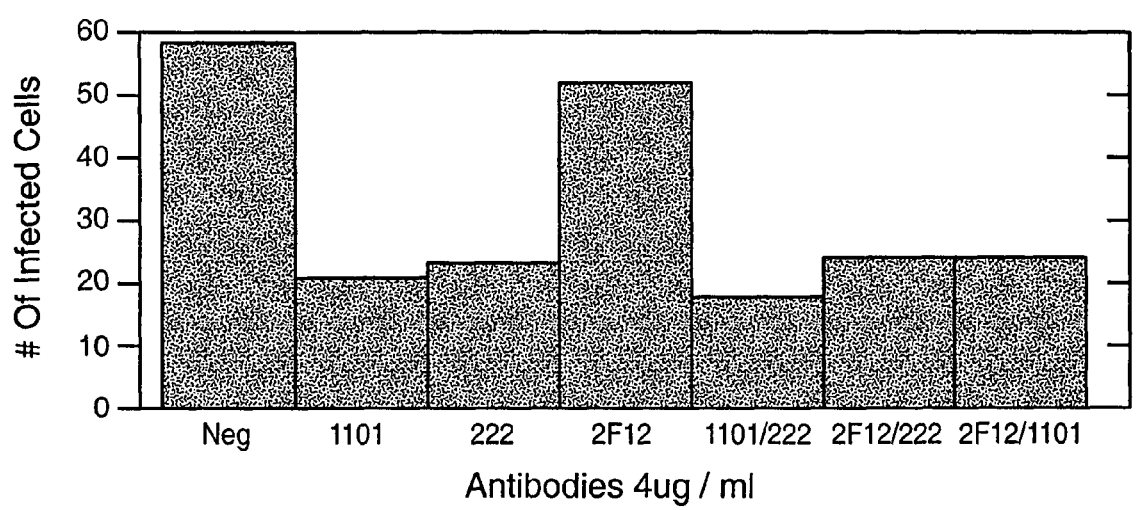
FIG._7

SEQUENCE LISTING

```
<160> NUMBER OF SEQ ID NOS: 6

<210> SEQ ID NO 1
<211> LENGTH: 1380
<212> TYPE: DNA
<213> ORGANISM: Cryptosporidium parvum

<400> SEQUENCE: 1
gaattcggca cgagaattac catctgatag atcaaattta cttacatcta tttttactac      60
attaaatatg gaggaaaaac agtcaatgag caatccacaa tcgaaaaata cgaatacaag     120
caataccaac cacaaagatt ctggtttaaa tgataaaata tttgaaatga ttacagatga     180
attcaaaaaa ttgacctta  gcttgtccaa agaattaaat gattcggttt cttcagcaat     240
tagcaagtat ttagaaccga tcgaacgtga tatacatcta ttaagtcgca tttgtcagga     300
atcgagaagt ctgttgataa ttatgttaat atcaatgaaa tttctaaaat tgaaacaaat     360
gttaaggaac ttcttacaag tacaaatgag aaattaacaa gcatcgacac ttgtatttcg     420
aggcttgttg gcgaatctag aagcgttcgt gaaaaagtga ctaaattaaa taaacaatgc     480
gataacatta actcgaatcc aatagacaac tttactcaag tagtagcaga ttcatttggg     540
acattaacta atgcagttac tcaattgcaa acaactgtta atcgtttgga attacagatc     600
agtaatggaa taccactaaa aacgtcttac accagataac tcaattacaa taagagcgcc     660
```

-continued

```
ccaaaacata gctttgcaaa ttgatgatgc cttaaaccaa acattacga tcggcatttc      720 ggatagcaat tctggatcaa tctaactcta tctcaatcag ataagagaga aatccaagcg      780
gagaatgttt tgttttgaac cttgcatata agtttgaccc atgtgtttgg ttggatgatc      840
cagcttccta ttagccatcc agtaatatta ggaatttcaa aaattttgag cgatactctt      900
cctcatttaa ttgaatcttt aaagaccagc tgtaattttt ctcaaattag ctgcatttca      960
gatttaaaat tgagaatatt atggataaaa gaaaccattc actgttttga accatttact     1020
gatactctta cacctagtga gtaatgcaaa tactaaatga aatttcagaa gtatgaacaa     1080
atgcattagc attataaatt cggttagcga tgcaagtaaa agcatgaact atattgtacc     1140
tgcatgcttc acgatgggt cgatcatcag tgatattact agcatattaa ggcatattag      1200
aaggacaact agaaatatta catctggaat gaaataaatt aataagggt agaattagat      1260 attttttcatg taaataaatt agcgttattg aggattattc gaaataaata atagagatat    1320
taagtttagt ttttatttaa aaaaaaaaaa aaaaaaaaaa aaaaaaaaaa aaaactcgag     1380
```

<210> SEQ ID NO 2
<211> LENGTH: 129
<212> TYPE: PRT
<213> ORGANISM: Cryptosporidium parvum

<400> SEQUENCE: 2

```
Ala Arg Glu Leu Pro Ser Asp Arg Ser Asn Leu Leu Thr Ser Ile Phe
1               5                   10                  15

Thr Thr Leu Asn Met Glu Glu Lys Gln Ser Met Ser Asn Pro Gln Ser
            20                  25                  30

Lys Asn Thr Asn Thr Ser Asn Thr Asn His Lys Asp Ser Gly Leu Asn
        35                  40                  45

Asp Lys Ile Phe Glu Met Ile Thr Asp Glu Phe Lys Lys Leu Thr Phe
    50                  55                  60

Ser Leu Ser Lys Glu Leu Asn Asp Ser Val Ser Ser Ala Ile Ser Lys
65                  70                  75                  80

Tyr Leu Glu Pro Ile Glu Arg Asp Ile His Leu Leu Ser Arg Ile Cys
                85                  90                  95

Gln Glu Ser Arg Ser Leu Leu Ile Ile Met Leu Ile Ser Met Lys Phe
            100                 105                 110

Leu Lys Leu Lys Gln Met Leu Arg Asn Phe Leu Gln Val Gln Met Arg
        115                 120                 125

Asn
```

<210> SEQ ID NO 3
<211> LENGTH: 1323
<212> TYPE: DNA
<213> ORGANISM: Cryptosporidium parvum

<400> SEQUENCE: 3

```
gaattcggca cgagattttt ttttttcttt tacctatttc aattagtttc tttgattcaa       60
acgatgcaaa gtcattattt gttttaaatc cagatggatc cggaattttg aaaaacattt      120
ctactaaatt cgaaattaaa tttgagcttg gcttgataaa tggtagttgg ctcggaggtg      180 atattttat ccttgatagg aaacacgctc ttgaagctgt aagttattca atcgcttgtg      240
ttttctatac aaaaacatgt tttgaaagaa tgaagcaca ttgtcttaaa cccttttaatc      300 gcgctgagaa taaaatgact tttggttctg agaaagactt agcgacaact ctccaatctt      360
```

```
ctaattctga atattatctt ttccttacat ggaataactg cattcttgga tatattccaa      420
ttaacacaaa taaaatcaac aaaatttctc ttgaaagttc cggagaaaac tcaatctcca      480
caattggata ttggagtatt atcgatggat tttcttcttc tttaattaaa catgcgccta      540
taaaagaaaa tggccacttg aataatcaag aatcaaaata ttcaaaatga ataatgaag       600 ccactaaact caacaaatcc agaatcaggt gggaataact taactcagaa ccaaaacaca      660
aagcctcatc cagttgttag accgcatcct acagaaaagc cctcaaatgg tgaacatcaa      720
gaatctggtt cagagcaagc ccctattacc tcaccagaaa acgaatcaag ttcaaatcat      780
ccttctgtga cagttccaga tactggatca gttcaaatct ccttctgtta ctattccaga      840
gactggatca gactcagatc acgcgccttg tgacaattcc agagactgga tcagttcaaa      900
tcatcttctg ctactatacc agaaacagga tccagctcag atcacactct gctacttctc      960
cagaagaagg attggactca gaacgttacc aatcacttct acagaacaaa ctcaaagcca     1020
gctacatatc taaccaaga aatgaaaat cataataatc aggaaggtaa ttcgagtttt       1080
aatacactaa atcttccaaa tcaacccaat cttcacgca agctggcaga tgtggaaagt      1140
tatggggaaa aggataaaat ggttgatggt gagcaagtaa tcactaaaaa tgacattatt     1200
gaagatactt cgaaagaaat tagaaacaaa atgtaaagta tctgcattga taaatatggc     1260
cttagccatt tccaaatatc taaattgtca actcaagtaa aaaaaaaaaa aaaaaaactc     1320
gag                                                                  1323

<210> SEQ ID NO 4
<211> LENGTH: 193
<212> TYPE: PRT
<213> ORGANISM: Cryptosporidium parvum

<400> SEQUENCE: 4

His Glu Ile Phe Phe Phe Leu Leu Pro Ile Ser Ile Ser Phe Phe Asp
1               5                   10                  15

Ser Asn Asp Ala Lys Ser Leu Phe Val Leu Asn Pro Asp Gly Ser Gly
                20                  25                  30

Ile Leu Lys Asn Ile Ser Thr Lys Phe Glu Ile Lys Phe Glu Leu Gly
            35                  40                  45

Leu Ile Asn Gly Ser Trp Leu Gly Gly Asp Ile Phe Ile Leu Asp Arg
        50                  55                  60

Lys His Ala Leu Glu Ala Val Ser Tyr Ser Ile Ala Cys Val Phe Tyr
65                  70                  75                  80

Thr Lys Thr Cys Phe Glu Lys Asn Glu Ala His Cys Leu Lys Pro Phe
                85                  90                  95

Asn Arg Ala Glu Asn Lys Met Thr Phe Gly Ser Glu Lys Asp Leu Ala
            100                 105                 110

Thr Thr Leu Gln Ser Ser Asn Ser Glu Tyr Tyr Leu Phe Leu Thr Trp
        115                 120                 125

Asn Asn Cys Ile Leu Gly Tyr Ile Pro Ile Asn Thr Asn Lys Ile Asn
130                 135                 140

Lys Ile Ser Leu Glu Ser Ser Gly Glu Asn Ser Ile Ser Thr Ile Gly
145                 150                 155                 160

Tyr Trp Ser Ile Ile Asp Gly Phe Ser Ser Leu Ile Lys His Ala
                165                 170                 175

Pro Ile Lys Glu Asn Gly His Leu Asn Asn Gln Glu Ser Lys Tyr Ser
            180                 185                 190

Lys
```

```
<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
gtcatatggc acgagaatta ccatctgat                                       29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
gacatatgtt aatttctcat ttgtacttg                                       29
```

CRYPTOSPORIDIUM PARVUM ANTIGENS, ANTIBODIES THERETO AND DIAGNOSTIC AND THERAPEUTIC COMPOSITIONS THEREOF

CROSS-REFERENCE TO RELATED APPLICATIONS

This application is a continuation of U.S. patent application Ser. No. 10/948,490, filed Sep. 23, 2004, which is a continuation of U.S. patent application Ser. No. 09/881,556, filed Jun. 14, 2001 (now U.S. Pat. No. 6,808,900) from which priority is claimed pursuant to 35 U.S.C §120, and claims benefit under 35 U.S.C. §119(e) of U.S. Provisional Patent Application No. 60/212,083, filed Jun. 15, 2000, which applications are hereby incorporated by reference in their entireties.

TECHNICAL FIELD

The present invention relates generally to protozoan antigens and genes encoding the same. More particularly, the present invention pertains to the cloning, expression and characterization of polypeptides from *Cryptosporidium parvum* (*C. parvum*) and antibodies directed to these polypeptides. The invention also pertains to use of the antigenic polypeptides and antibodies in therapeutic and diagnostic compositions.

BACKGROUND

*Cryptosporidium parvum* (*C. parvum*) is a coccidian protozoan that infects a wide variety of vertebrates, including humans. *C. parvum* can be acquired directly from animal-to-human contact, human-to-human contact or indirectly in fomites, water and sometimes food. Current et al. (1983) *N. Engl. J. Med.* 308:1252-1257; Centers of Disease Control (1984) "Cryptosporidiosis among children attending daycare centers—Georgia, Pennsylvania, Michigan, California, New Mexico" 33:599-601; Wolfson et al. (1995) *N. Engl. J. Med.* 312:1278-1281. Acquisition of infection occurs by ingestion of oocysts which excyst in the upper small bowel releasing four infective sporozoites. The sporozoites penetrate the lining enterocyte and undergo either sexual or asexual reproduction, gametogony and merogony, respectively. The products of either form of reproduction are capable of sustaining infection in man. Navin et al. (1984) *Rev. Infect. Dis.* 6:313-327.

The reservoir of *C. parvum* is in wild and domestic animals, particularly cattle (Tzipori (1983) *Microbiol. Rev.* 47:84-96) and this pathogen causes significant economic losses to the farm industry annually. Clinical manifestations of *C. parvum* infection may include watery diarrhea, crampy epigrastric abdominal pain, malabsorption of nutrients and weight loss, anorexia and malaise. The disease is usually self limited in the immunocompetent host but can be life threatening in the immunodeficient host, particularly in human patients with advanced Human Immunodeficiency Virus (HIV) infection. Current et al. (1983), supra; Wolfson et al. (1985) *N. Engl. J. Med.* 312:1278-1281; Soave (1988) *Infect. Dis. Clin. N. Amer.* 2:485.

The absence of an adequate in vitro culture system has severely limited the investigation of *C. parvum*. Furthermore, use of animal models, particularly mice, is of limited value because adult mice are not normally susceptible to infection with *C. parvum*.

Several groups have reported the cloning and characterization of *C. parvum* antigens and genes using a variety of techniques. See, e.g., Jenkins et al. (1993) *Infect. Immun.* 61:2377-2382; Jenkins et al. (1995) *Mol. Biochem. Parasitol.* 71:149-152; Peterson et al. (1992) *Infect. Immun.* 60:2343-2348; Ranucci et al. (1993) *Infect. Immun.* 61:2347-2356.

After natural infection, a wide variety of cryptosporidial proteins are recognized by human and animal immune sera. Ortega-Mora et al. (1992) *Infect. Immun.* 60:3442-3445; Campbell et al. (1983) *J. Clin. Microbiol.* 18:165-169; Whitmire et al. (1991) *Infect. Immun.* 59:990-995; Nina et al. (1992) *Infect. Immun.* 60:1509-1513; Peeters et al. (1992) *Infect. Immun.* 60:2309-2316. The components that constitute protective immunity are unknown although, like most obligate intracellular coccidian protozoa, both the cellular and humoral arms of the immune response are likely to play important roles in the genesis of protective immunity. Lillehoj et al. (1994) *Parasit. Today* 10:10-16. Use of recombinant *C. parvum* proteins in vaccine compositions has also been described. See, e.g., U.S. Pat. No. 5,591,434. However, no consistently effective therapy of vaccination exists, perhaps because the antigens used in the vaccines were identified from non-human sources.

There have also been several attempts to identify antibodies that neutralize *C. parvum* infection. In human studies, orally administered hyperimmune bovine colostrum has been found to alter the natural history of *C. parvum* by decreasing the excretion of oocysts, reducing the level of diarrhea, and in a smaller number of cases, clearing the parasite from stool. Tzipori et al. (1986) *Br. Med. J.* 293:1276-1277; Nord et al. (1989) "Treatment of AIDS associated cryptosporidiosis with hyperimmune colostrum from cows vaccinated with *Cryptosporidium*", Fifth International Conference on AIDS, Montreal, Quebec, May 1989; Ungar et al. (1990) *Gastroenterology* 98:486-489. Several antigens that are recognized by sera after natural infection have been characterized and have been shown to be the targets of neutralizing antibody in the murine system. Arrowood et al. (1989) *Infect. Immun.* 57:2283-2288; Bjorneby et al. (1991) *Infect. Immun.* 59:1172-1176; Doyle et al. (1993) *Infect. Immun.* 61:4079-4084; Riggs et al. (1989) *J. Immunol.* 143:1340-1345; Peterson et al. (1992) *Infect. Immun.* 60:2343-2348. However, animal studies in the murine model of infection indicate only a partially protective role when these antibodies are orally administered.

Thus, there remains a need for the identification of antibodies useful in diagnostic and therapeutic compositions and for the identification of antigens from *C. parvum* that react with human sera and for diagnostic and therapeutic compositions and methods using these antigens.

DISCLOSURE OF THE INVENTION

The present invention is based on the discovery of genes encoding *C. parvum* antigenic polypeptides, the characterization of these polypeptides and antibodies that recognize epitopes of these polypeptides. The proteins encoded by the genes have been recombinantly produced and these polypeptides, immunogenic fragments and analogs thereof, and/or chimeric proteins including the same, can be used, either alone or in combination with other *C. parvum* antigens, in novel subunit vaccines to provide protection from cryptosporidial infection in mammalian subjects. Antibodies generated against these proteins, and/or fragments thereof, either alone or in combination with other therapeutic agents, can be used in novel therapeutic agents for mammalian subjects. Furthermore, the antigens and antibodies can be used as diagnostics.

Accordingly, in one embodiment, the subject invention is directed to an isolated nucleic acid molecule comprising a coding sequence for an immunogenic *C. parvum* antigenic polypeptide selected from the group consisting of (a) a *C. parvum* antigenic polypeptide AG1 and (b) a *C. parvum* antigenic polypeptide AG2, or a fragment of the nucleic acid molecule comprising at least 15 nucleotides.

In additional embodiments, the invention is directed to recombinant vectors including the nucleic acid molecules, host cells transformed with these vectors, and methods of recombinantly producing *C. parvum* antigenic polypeptides.

In still further embodiments, the subject invention is directed to vaccine compositions comprising a pharmaceutically acceptable vehicle and an immunogenic *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, as well as methods of preparing the vaccine compositions.

In other embodiments, the invention is directed to therapeutic compositions comprising a pharmaceutically acceptable vehicle and an antibody (e.g. monoclonal antibody 1101 or 222) that recognize an immunogenic *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, as well as methods of preparing the therapeutic compositions.

In yet other embodiments, the present invention is directed to methods of treating or preventing *C. parvum* infections in a mammalian subject. The method comprises administering to the subject a therapeutically effective amount of the above vaccine or therapeutic compositions.

In additional embodiments, the invention is directed to methods of detecting *C. parvum* antibodies in a biological sample comprising:
(a) providing a biological sample;
(b) reacting the biological sample with a *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, under conditions which allow *C. parvum* antibodies, when present in the biological sample, to bind to the *C. parvum* antigenic polypeptide to form an antibody/antigen complex; and
(c) detecting the presence or absence of the complex,
thereby detecting the presence or absence of *C. parvum* antibodies in the sample.

In additional embodiments, the invention is directed to methods of detecting *C. parvum* antigens in a biological sample comprising:
(a) providing a biological sample;
(b) reacting the biological sample with an antibody that recognizes a *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, under conditions which allow *C. parvum* antigens, when present in the biological sample, to bind to the *C. parvum* antibody to form an antibody/antigen complex; and
(c) detecting the presence or absence of the complex,
thereby detecting the presence or absence of *C. parvum* antigens in the sample.

In yet further embodiments, the invention is directed to an immunodiagnostic test kit for detecting *C. parvum* infection. The test kit comprises a *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, and instructions for conducting the immunodiagnostic test. The invention is also directed to immunodiagnostic test kits comprising an antibody that recognizes a *C. parvum* antigenic polypeptide selected from the group consisting of (a) a *C. parvum* antigenic polypeptide AG1, (b) a *C. parvum* antigenic polypeptide AG2 and (c) an immunogenic fragment of (a) or (b) comprising at least 5 amino acids, and instructions for conducting the immunodiagnostic test.

These and other embodiments of the present invention will readily occur to those of ordinary skill in the art in view of the disclosure herein.

BRIEF DESCRIPTION OF THE FIGURES

FIGS. 1A-1B show the nucleotide sequence (SEQ ID NO:1) and corresponding amino acid sequence (SEQ ID NO:2) of *C. parvum* AG1.

FIGS. 2A-2B show the nucleotide sequence (SEQ ID NO:3) and corresponding amino acid sequence (SEQ ID NO:4) of *C. parvum* AG2.

FIGS. 3A and 3B show immunoblots of affinity purified human antibodies and monoclonal antibody 1101 directed against total, soluble and insoluble cryptosporidial proteins. FIG. 3A shows that human antibodies recognize a faint band in total protein at approximately 22 kDa Monoclonal antibody 1101 recognized a 22 kd band (FIG. 3B, lane 1) in insoluble cryptosporidial protein and FIG. 3B, lane 2 shows that 1101 recognized three bands (22, 32 and 96 kDa) in soluble cryptosporidial protein.

FIGS. 4A and 4B show immunoblots of affinity purified human antibodies and monoclonal antibody 222 directed against total, soluble and insoluble cryptosporidial proteins. FIG. 4A shows that human antibodies recognize three bands in total protein at approximately 17, 34 and 84 kDa. Monoclonal antibody 222 recognized no bands (FIG. 4B, lane 1) in insoluble cryptosporidial protein and five bands at approximately 6, 10, 22, 34 and 84 kDa in soluble cryptosporidial protein. (FIG. 4B, lane 2).

FIGS. 5A-5F show immunolocalization in *C. parvum* oocysts and sporozoites of antigens recognized by mAbs 1101, 222 and JB1. FIG. 5A shows that JB1 (directed again human integrin) non-specifically labeled slide preparations. FIG. 5B shows that mAb 1101 (directed against AG1) intensely stained in a diffuse pattern single and pairs of oocysts. FIG. 5C shows that mAb 222 (directed against AG2) stained single oocysts and clumps in a ring-like pattern. FIG. 5D shows that sporozoites were not visualizable when stained with JB1. FIG. 5E shows that mAb 1101 stained sporozoites in an even staining pattern and FIG. 5F shows that mAb 222 detected sporozoites with an intense pattern.

FIG. 6 depicts the effect of increasing concentrations of mAbs 1101 and 222 compared to control mAb 2F12 on sporozoite invasion of HT-29 cells.

FIG. 7 depicts the effect of combinations of mAbs 1101 and 222 on sporozoite invasion of HT-29 cells.

DETAILED DESCRIPTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory*

Manual, Vols. I, II and III, Second Edition (1989); Perbal, B., *A Practical Guide to Molecular Cloning* (1984); Harlow, E., et al., *Antibodies: A Laboratory Manual*, Cold Spring Harbor Press, Cold Spring Harbor, N.Y. (1988); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (O)
Glutamic acid: Glu (E) Glycine: Gly (G)
Histidine: H is (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

A. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a *C. parvum* polypeptide" includes a mixture of two or more such proteins, and the like. Furthermore, the derived polypeptide or nucleotide sequences need not be physically derived from the organism or gene of interest, but may be generated in any manner, including for example, chemical synthesis, isolation (e.g., from *C. parvum*) or by recombinant production, based on the information provided herein. Additionally, the term intends proteins having amino acid sequences substantially homologous (as defined below) to contiguous amino acid sequences encoded by the genes, which display immunological activity and/or are recognized by a biological sample obtained from an infected subject.

Thus, the terms "polypeptide" and "protein" are used interchangeably to intend full-length, as well as immunogenic, truncated and partial sequences, and active analogs and precursor forms of the polypeptides. Similarly, the terms "polynucleotide" and "nucleotide sequence" are used interchangeably to intend nucleotide fragments of the gene that include at least about 8 contiguous base pairs, more preferably at least about 10-20 contiguous base pairs (or any value therebetween), and most preferably at least about 25 to 50 (or any value therebetween), or more, contiguous base pairs of the gene. Such fragments are useful as probes and in diagnostic methods, discussed more fully below.

The terms also include polypeptides in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The polypeptide and polynucleotides of the invention therefore encompass deletions, additions and substitutions to the sequence, so long as the polypeptide product functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide. For example, molecules having between about 20 and 15 substitutions per 100 amino acids, or less than about 10 substitutions per 100 amino acids, or between about 5 and 3 substitutions per 100 amino acids that retain their biological activity (e.g., immunogenicity) are within this definition.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host and/or a quicker recovery time.

The terms "immunogenic" protein or polypeptide refer to an amino acid sequence which elicits an immunological response as described above. An "immunogenic" protein or polypeptide, as used herein, includes the full-length sequence of the *C. parvum* polypeptides in question, with or without any signal sequences, membrane anchor domains, analogs thereof, or immunogenic fragments thereof. By "immunogenic fragment" is meant a fragment of which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic fragments, for purposes of the present invention, will usually include at least about 3 amino acids, preferably at least about 5 amino acids, more preferably at least about 10-15 amino acids, and most preferably 25 or more amino acids, of the parent *C. parvum* antigenic molecule. There is no critical upper limit to the length of the fragment, which may comprise nearly the full-length of the protein sequence, or even a fusion protein comprising two or more epitopes of AG1 and/or AG2.

"Native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent identity between two polynucleotide or two polypeptide moieties. Two nucleotide, or two polypeptide sequences, are "substantially homologous" to each other when the sequences exhibit at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

Techniques for determining nucleic acid and amino acid "sequence identity" or "sequence homology" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used to determine percent identity using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. Another example of determining percent identity is using the Smith-Waterman search algorithm (Time Logic, Incline Village, Nev.), with the following exemplary parameters: weight matrix=nuc4×4hb; gap opening penalty=20, gap extension penalty=5.

Alternatively, for nucleotides, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. For example, stringent hybridization conditions can include 50% formamide, 5×Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra; *DNA Cloning*, supra; *Nucleic Acid Hybridization*, supra. For amino acids, homology can also be determined by aligning two or more amino acids sequences (as described above) and determining the number of substitutions and/or deletions. Typically, amino acid sequences are substantially homologous when between about 20 and 15 amino acid substitutions or deletions are made per 100 amino acids, more preferably between about 10 amino acid substitutions or deletions and even more preferably between about 5 and 3 amino acid substitutions or deletions. As used herein, substantially homologous also refers to sequences showing complete identity to the specified DNA or polypeptide sequence.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

The term "functionally equivalent" intends that the amino acid sequence of an antigenic *C. parvum* polypeptide is one that will elicit a substantially equivalent or enhanced immunological response, as defined above, as compared to the response elicited by an antigenic polypeptide having identity with the AG1 and AG2 polypeptides, or immunogenic portions thereof. The term also includes antibodies, or fragments thereof, that will elicit a substantially equivalent or enhanced neutralizing or other therapeutic response, as compared to monoclonal antibodies 1101 and 222. "1101" refers to a particular monoclonal antibody raised against the antigenic *C. parvum* polypeptide with the designation AG1. The generation and characterization of 1101 is described in the Examples. Similarly, "222" refers to a particular monoclonal antibody raised against the antigenic *C. parvum* polypeptide with the designation AG2. The generation and characterization of 222 is described in the Examples.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The terms "treatment" and "therapeutic" as used herein refer to either (i) the prevention of infection or reinfection (prophylaxis), including, for example, vaccines or (ii) the reduction or elimination of symptoms of the disease of interest (therapy).

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and $\alpha$-$\beta$-galactosidase.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species.

B. GENERAL METHODS

Central to the present invention is the discovery of genes encoding two *C. parvum* antigenic polypeptides (termed "AG1" and "AG2" respectively herein) and antibodies to these polypeptides which have been shown to have neutralizing effects on *C. parvum* infection in mammalian subjects. In particular, the genes for *C. parvum* antigenic polypeptide 1 ("ag1") and *C. parvum* antigenic polypeptide 2 ("ag2") have been isolated, sequenced and characterized, and the protein sequences for AG1 and AG2 deduced therefrom. Monoclonal antibodies have been generated against the recombinantly produced proteins and have been shown to have neutralizing activity against the infective sporozoite of *C. parvum*.

The cDNA and predicted amino acid sequences of AG1 and AG2 are shown in FIGS. 1A-1B and 2A-2B, respectively. Perfect and imperfect consensus polyadenylation signals are underlined and N-glycosylation sites are in bold face type. The DNA sequence of AG1 is also shown in SEQ ID NO: 1, while SEQ ID NO: 3 shows the complete DNA sequence of AG2. The predicted amino acid sequences for AG1 and AG2 are shown in SEQ ID NO: 2 and SEQ ID NO: 4, respectively.

As described in the examples, full-length ag1, depicted at nucleotide positions 8-394, inclusive, of FIG. 1A, encodes a full-length AG1 protein of approximately 129 amino acids, shown as amino acids 1-129, inclusive, of FIG. 1A (SEQ ID NO: 2). The 3' untranslated region is 945 nucleotides long, from positions 395-1338 of FIGS. 1A-1B (SEQ ID NO: 1). Imperfect polyadenylation signals occur at positions 1241-1245 and 1307-1311. The sequence (SEQ ID NO: 1) has been assigned GenBank Accession Number AF178459. The protein encoded by the predicted open reading frame (ORF) has a predicted molecular weight of about 15 kDa. The predicted isoelectric point is pH 9.6 and 44% of the predicted amino acid residues are hydrophobic. Two N-linked glycosylation sites have been identified at amino acid residues 36-38 and 71-73.

Full-length ag2, depicted at nucleotide positions 9-587, inclusive, of FIG. 2A, encodes a full-length AG2 protein of approximately 193 amino acids, shown as amino acids 1-193, inclusive, of FIG. 2A (SEQ ID NO: 4). The 3' untranslated region is 712 nucleotides long, from positions 588-1298 of FIGS. 2A-2B (SEQ ID NO: 4). Imperfect polyadenylation signals occur at positions 945-949 and 1141-1145. The sequence (SEQ ID NO: 3) has been assigned GenBank Accession Number AF178460. The protein encoded by the predicted open reading frame (ORF) has a predicted molecular weight of about 21.8 kDa. The predicted isoelectric point is pH 6.23 and 36% of the predicted amino acid residues are hydrophobic. Two N-linked glycosylation sites were identified at amino acid residues 36-38 and 51-53.

The *C. parvum* polynucleotides, antigenic peptides, immunogenic fragments thereof or chimeric proteins including one or more epitopes of AG1 and AG2, can be provided, either alone or in combination, in subunit vaccine compositions or other therapeutic compositions to treat or prevent infections caused by *C. parvum*. Similarly, antibodies generated to AG1 or AG2, for example, monoclonal antibodies 1101 and 222, and antibodies cross-reactive therewith, can be provided, alone or in combination, in compositions to prevent, treat, or neutralize infections caused by *C. parvum*.

In addition to use in therapeutic compositions, proteins and fragments thereof, antibodies thereto, and polynucleotides coding therefor, can be used as diagnostic reagents to detect the presence of infection in a mammalian subject. Similarly, the polynucleotides encoding the proteins can be cloned and used to design probes to detect and isolate homologous genes in other protozoans. For example, fragments comprising at least about 15-20 nucleotides, more preferably at least about 20-50 nucleotides, and most preferably about 60-100 or more nucleotides, will find use in these embodiments. The *C. parvum* antigenic polypeptides also find use in purifying antibodies for diagnostic and therapeutic uses.

*C. parvum* antigenic polypeptides can be used in vaccine compositions either alone or in combination with bacterial, fungal, viral or other protozoal antigens. These antigens can be provided separately or even as fusion proteins comprising one or more epitopes of the antigenic polypeptides fused together and/or to one or more of the above antigens. For example, other immunogenic proteins from *C. parvum* can be used in the subject therapeutic compositions. Antibodies directed to these polypeptides can also be used as therapeutics. Antibodies 1101 and 222 have each been shown to have a neutralizing effect on *C. parvum* infection.

Production of Antigenic Polypeptides

The above described antigenic polypeptides and active fragments, analogs and chimeric proteins derived from the same, can be produced by a variety of methods. Specifically, the polypeptides can be isolated directly from protozoa (oocytes, sporozoites or adults) which express the same, using standard purification techniques. See, e.g. Tilley et al. (1991) *Infect. Immun.* 59:1002-1007. The desired proteins can then be further purified i.e. by column chromatography, HPLC, immunoadsorbent techniques or other conventional methods well known in the art.

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for *C. parvum* or another pathogen).

The ag1 and ag2-encoding sequences of the present invention can be isolated based on the ability of the protein products to bind to antibodies present in an infected sample, using detection assays as described below. Thus, gene libraries can be constructed and the resulting clones used to transform an appropriate host cell. Colonies can be pooled and screened for clones having the ability to bind *C. parvum* antibodies. Colonies can be screened using polyclonal serum or monoclonal antibodies to the *C. parvum* proteins.

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. 1, supra; *Nucleic Acid Hybridization*, supra; Oligonucleotide Synthesis, supra; Sambrook et al., supra. Once a clone from the screened library has been identified by positive hybridization, it can be confirmed by restriction enzyme analysis and DNA sequencing that the particular library insert contains a sequence encoding an antigenic *C. parvum* polypeptide or a homolog thereof. The sequences can then be further isolated using standard techniques and, if desired, PCR approaches or restriction enzymes employed to delete portions of the full-length sequence.

Similarly, genes can be isolated directly from protozoans using known techniques, such as phenol extraction and the sequence further manipulated to produce any desired alterations. See, e.g., Sambrook et al., supra, for a description of techniques used to obtain and isolate DNA.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. For example, the signal sequence for the particular *C. parvum* antigenic polypeptide, can be used for secretion thereof, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the antigenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

Production of Antibodies

The antigenic polypeptides of the present invention, or their fragments, can be used to produce antibodies, both polyclonal and monoclonal. In addition to whole antibody molecules, antibody fragments retaining the immunological specificity of the whole antibody may also be used in the practice of the present invention (e.g., Fab and F(ab')₂ fragments of IgG (Pierce)). The antibodies can be purified by standard methods to provide antibody preparations which are substantially free of serum proteins that may affect reactivity (e.g., affinity purification (Harlow et al.)). If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363-370. If serum containing polyclonal antibodies is used, the polyclonal antibodies can be purified by immunoaffinity chromatography, using known procedures.

Monoclonal antibodies to the antigenic polypeptides and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigenic polypeptides, or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Antibodies exhibiting a neutralizing effect on *C. parvum*, for example monoclonal antibodies 1101 and 222 described below, and others functionally equivalent to these antibodies, are also useful in therapeutic compositions. Polyclonal and monoclonal antibodies are also useful for diagnostic purposes.

Therapeutic Formulations and Administration

The polynucleotides, antigenic *C. parvum* polypeptides and antibodies thereto of the present invention can be formulated into compositions or for use as diagnostics, either alone, in combination and/or with other polynucleotides, antigens and/or antibodies, for use in immunizing or treating subjects as described below. Methods of preparing such formulations are described in, e.g., *Remington's Pharmaceutical Sciences*, Mack Publishing Company, Easton, Pa., 18 Edition, 1990. Typically, therapeutic (e.g., vaccine) compositions of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active (e.g., immunogenic) ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine or other therapeutic composition may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

The antigenic polypeptides may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles. Antibodies and polynucleotides may also be linked to such carriers prior to administration.

The polynucleotides, antigenic polypeptides or antibodies thereto may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Other suitable carriers include cells, such as lymphocytes, since presentation in this form mimics the natural mode of presentation in the subject, which gives rise to the immunized state. Alternatively, the molecules of the present invention may be coupled to erythrocytes, preferably the subject's own erythrocytes. Methods of coupling peptides to proteins or cells are known to those of skill in the art.

Furthermore, the antigenic polypeptides (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

These formulations will typically contain a "therapeutically effective amount" of the active ingredient, that is, an amount capable of eliciting an immune response or capable of eliciting a neutralizing response, in a subject to which the composition is administered. In the treatment and prevention of *C. parvum* infection, for example, a "therapeutically effective amount" would preferably be an amount that enhances resistance of the mammal in question to new infection and/or reduces the clinical severity of the disease. Such protection will be demonstrated by either a reduction or lack of symptoms normally displayed by an infected host and/or a quicker recovery time.

The exact amount is readily determined by one skilled in the art using standard tests and in view of the teachings of the specification. The antigenic polypeptide, antibody concentration or polynucleotide concentration will typically range from about 1% to about 95% (w/w) of the composition, or even higher or lower if appropriate. Typically, vaccine formulations will contain between about 1 ug to 1 mg per vaccination dose, although more or less may be used if needed.

Repeat vaccination (e.g., boosts) can be administered as deemed necessary, for example by evaluation of reactive T-cells.

To immunize a subject, the vaccine is generally administered parenterally, usually by intramuscular injection. Intradermal and transdermal modes of administration may also be employed. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered using as many doses as is required to maintain a state of immunity to infection. Similarly, for other therapeutic compositions, the polypeptides and/or antibodies can be administered by injection (intramuscular, intradermal intraperitoneal, intravenous, etc.)

Additional therapeutic formulations which are suitable for other modes of administration include suppositories and, in some cases, aerosol, transdermal, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the polynucleotide and/or protein (e.g., antigenic polypeptide or antibody) into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The antigenic polypeptides can also be delivered using implanted minipumps, well known in the art.

The polynucleotides, antigenic polypeptides and/or antibodies of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK recombinant can be selected by culturing the cells in the presence of 5-bromodeoxyuridine and picking viral plaques resistant thereto.

Thus, one route of administration involves nucleic acid immunization. Thus, nucleotide sequences (and accompanying regulatory elements) encoding the subject antigenic polypeptides and/or antibodies or fragments thereof can be administered directly to a subject for in vivo translation thereof. Alternatively, gene transfer can be accomplished by transfecting the subject's cells or tissues ex vivo and reintroducing the transformed material into the host. Nucleic acids (e.g., DNA and RNA) can be directly introduced into the host organism, i.e., by injection (see U.S. Pat. Nos. 5,580,859 and 5,589,466; International Publication No. WO/90/11092; and Wolff et al. (1990) *Science* 247:1465-1468). Liposome-mediated gene transfer can also be accomplished using known methods. See, e.g., U.S. Pat. No. 5,703,055; Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219 A; and Nabel et al. (1990) *Science* 249:1285-1288. Targeting agents, such as antibodies directed against surface antigens expressed on specific cell types, can be covalently conjugated to the liposomal surface so that the nucleic acid can be delivered to specific tissues and cells susceptible to infection. As noted above, nucleic acid formulations can be administered by any suitable mode, for example, intramuscularly, intradermally or transdermally.

Diagnostic Assays

As explained above, the polynucleotides and/or antigenic polypeptides of the present invention may also be used as diagnostics to detect the presence of reactive antibodies of *C. parvum* in a biological sample in order to determine the presence of *C. parvum* infection. For example, the presence of antibodies reactive with antigenic polypeptides can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation; etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more antigenic polypeptides) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a antigenic polypeptide. A biological sample containing or suspected of containing anti-antigenic polypeptide immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-*C. parvum* antigen ligands from a biological sample can be readily detected using a secondary binder comprising an antibody directed against the antibody ligands. A number of anti-mammalian immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antigenic polypeptides and antibodies specific for those proteins form complexes under precipitating conditions. In one particular embodiment, antigenic polypeptides can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the antigenic polypeptides. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-*C. parvum* molecules is immobilized to a substrate. In this regard, an initial affinity purification of the sample can be carried out using immobilized antigens. The resultant sample preparation will thus only contain anti-*C. parvum* moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled antigenic polypeptides are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the antigenic polypeptides, rather than the antigenic polypeptides themselves, can be used in the above-described assays in order to detect the presence of antibodies to the proteins in a given sample. These assays are performed essentially as described above and are well known to those of skill in the art.

Assays specifically involving the polynucleotides of the present invention also include, but are not limited to, assays for alteration of mRNA levels and/or the presence of polynucleotides which selectively hybridize to the sequences described herein. In assay for an alteration in mRNA levels, nucleic acid contained in the samples (e.g., cell or tissue prepared from the subject) is first extracted according to standard methods, for example using lytic enzymes or chemical solutions according to the procedures set forth in Sambrook et al, supra or extracted by nucleic-acid-binding resins following the manufacturer's instructions. The extracted mRNA is then detected by hybridization (e.g., Northern blot analysis) and/or amplification (e.g., PCR). Nucleic acids having at least 10 nucleotides, preferably between about 20 and 25 nucleotides, even more preferably between about 50 and 100 nucleotides, and exhibiting sequence complementarity or homology to the polynucleotides described herein find utility as hybridization probes. It is understood that probes need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g., avidin/biotin). Further, the nucleic acids can also be attached to a solid support (e.g., glass or chip) for use in high throughput screening assays using methods described, for example, in U.S. Pat. Nos. 5,405,783, 5,578,832 and 5,445,934. Results of high throughput assays can be analyzed using computer software programs available from the manufacturers.

The above-described assay reagents, including the antigenic polypeptides, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Below are examples of specific embodiments for carrying out the present invention. The examples are offered for illustrative purposes only, and are not intended to limit the scope of the present invention in any way.

C. EXPERIMENTAL

Example 1

Isolation and Cloning of C. parvum ag1 and ag2

A. Collection of Oocysts

Neonatal calves were infected with a human isolate of C. parvum obtained from Cadham Provincial Laboratories (Winnipeg, MB, Canada) and the feces collected and stored in an equal volume of 2.5% potassium dichromate at 4° C. Oocysts were isolated from feces by sucrose floatation centrifugation followed by ultracentrifugation on cesium chloride step gradients as previously described in Taghi-Kilani et al. (1990) J. Immunol. 145:1571-1576. Purified oocysts were then stored at 4° C. for future use.

B. cDNA Expression Library Construction

RNA was extracted from oocysts using a guanidium isothiocyanate isolation procedure as previously described in Rajkovic et al. (1989) PNAS USA 86:8217-8221 and polyadenylylated RNA (poly A+) was isolated by oligo dT selection. Five ml of highly purified oocysts yielded approximately 4.8 mg of total RNA and about 20 μg of polyadenylylated RNA (poly A+ RNA) (mRNA) isolated using oligo dT selection (0.4%).

Five μg of poly A+ RNA was then converted to cDNAs according to the manufacturers instructions (Stratagene, La Jolla, Calif.). To construct the library, the cloning vector Lambda ZAP IIXROD® (Stratagene), a Lambda gt11 derivative containing the lacz gene (11-galactosidase) and lac promoter, was used. The cDNAs were ligated into the lambda arms, packaged in vitro and plated on E. coli strain SURE® Ligation efficiency was determined by blue/white color selection of plaques in the presence of 5-bromo-4-chloro-3-indoyl-11D-galctosidase (X-gal) and 2-isopropyl-b-D-thiogalactopyranoside (IPTG). This procedure yielded 2×10$^6$ primary phage of which 95% were demonstrated to be recombinant by blue-white colour selection in the presence of IPTG/X-gal.

C. Preparation of Human Immune Serum

Human immune serum was obtained from a patient who had a parasitologically documented infection. Antibodies directed against E. coli proteins were removed by preabsorption with a lysate of E. coli X-BLUE®-buffered saline (20 mM TRIS pH 7.5). Serum was diluted 1:200 with 0.1% BSA in Tris 500 mM NACl) and incubated overnight at 4° C. with shaking in the presence of 5 mg/ml of the host E. coli strain protein. The debris was pelleted and the supernatant removed. Immunoblots of C. parvum and E. coli were performed to ensure E. coli antibodies had been removed and C. parvum antibodies were still present (described below). This prepared immune sera was used in the subsequent screening of the cDNA library.

D. Immunoblotting of Proteins

Following electrophoresis on 10% SDS-PAGE, C. parvum, E. coli or recombinant cryptosporidial proteins were transferred (Transbiot SD Semi-dry Electrophoretic Transfer Cell/Bio-Rad, Mississauga, Ontario) onto Immobilon-P transfer membranes (Millipore, Bedford, Ma) according to the manufacturer instructions. Five percent (5%) skim milk in TRIS-buffered saline (TBS) was used to block the immunoblots for 2 hours at 37° C. and then incubated with immune sera diluted 1:200 or monoclonal antibodies diluted 1:2000 in 0.1% bovine serum albumin (BSA)/TBS for 2 hours at 37° C. The membranes were washed 3 times for 5 minutes each in 0.05% Tween-20 in TBS (TBST). IgG antibodies were detected using either goat anti-human or anti-mouse IgG conjugated to horseradish peroxidase (Jackson Immunoresearch Laboratories, West Grove, Pa.) diluted 1:3000 with 0.1% BSA/TBS for 2 hours at 37° C. Following another wash, blots were developed in 1.4 mM diaminobenzidine, 8.8 mM cobalt chloride and 0.85 mM hydrogen peroxide.

Immunoblots of C. parvum and E. coli proteins were performed with preabsorbed immune serum. Predominant bands were located at 23, 33, 45, and >66 kilodaltons, similar to the spectrum of antigens reported by other investigators. Antibodies against E. coli proteins were present in unabsorbed sera but were effectively removed by the absorption procedure leaving cryptosporidial specific antibodies intact.

E. Screening of the Expression Library

A cDNA expression library was screened as follows: approximately 2000 primary plaques per plate were incubated for four hours on Luria-Brunelli (LB) agar at 37° C. and the plates were overlaid with nitrocellulose filters (Millipore, Bedford, Mass.) presoaked in 10 mM IPTG and incubated for another four hours at 37° C. Filters were removed and duplicate filters were placed and allowed to incubate for four more hours. The filters were blocked in 5% skim milk in TBST and developed as described above for immunoblotting. Positive clones were plaque purified.

After library amplification, approximately 650,000 primary plaques were screened and eight positive clones identified. These were plaque purified and rescued by in vivo excision into the sequencing phagemid pbluescript SK+.

F. In Vivo Excision and Sequencing of C. parvum cDNA

Recombinant pBluescript SK+ containing the C. parvum cDNA was prepared by an in vivo excision protocol supplied by the manufacturer (Stratagene, La Jolla, Calif.). Plasmid DNA was prepared by established protocols. Insert cDNA was sequenced by the dideoxy method (Sequenase™, U.S. Biochemical, Cleveland, Ohio).

The cDNA inserts of the positive clones were completely sequenced. The eight positive clones encoded two distinct antigens, AG1 and AG2. The composite cDNA sequence of the inserts and the predicted open reading frames of the two antigens are presented in FIG. 1.

The incomplete open reading frame of AG1 deduced from a single cDNA and two overlapping cDNA clones extended from nucleotides 8-394. The 3' untranslated region was 945 nucleotides long and extended from positions 395-1338. Consensus polyadenylylation signals were located at nucleotides 1233-1238 and 1273-1278. Imperfect polyadenylylation signals were also identified at nucleotides 1241-1245 and 1307-1311. The predicted open reading frame encoded a peptide of 129 amino acids with a predicted molecular weight of 15 Kd. The predicted isoelectric point was Ph 9.6 with 44% of the amino acids being hydrophobic. Two N-linked glycosylation sites were identified at residues 36-38 and 71-73.

The incomplete composite open reading frame of AG2 deduced from five overlapping cDNA clones extended from nucleotides 9-587. The 3' untranslated region was 712 nucleotides in length and extended from nucleotides 588-1298. A number of imperfect consensus polyadenylylation signals were identified, for instance at nucleotides 945-949 and 1141-1145. The predicted open reading frame encoded a peptide of 193 amino acids in length with a predicted molecular weight of 21.8 Kd. The predicted isoelectric point is pH 6.23 and 36% of the amino acids were hydrophobic. Two N-linked glycosylation sites were identified at residues 36-38 and 51-53.

The GenBank database was searched using the BLAST program (see, e.g., Altschul et al. (1997) 25:3389-3402), using for example, the following gap penalties: existence: 11 or 5, extension: 1 or 2. Default parameters could also be used. The searches did not identify proteins that exhibit sequence identity with AG1 or AG2.

Example 2

Expression of the *C. parvum* cDNAs in *E. coli* and Analysis by Immunoblotting

Two different prokaryotic expression vector systems were used to generate recombinant protein, pGEX-2T™ (Pharmacia Biotech, Montreal, Canada) and pET-11A™ (Novagen, Madison, Wis.). The cDNA inserts of the two antigens (AG1 and AG2) were subcloned as a SmaI/XhoI end-filled fragment into the SmaI site of the pGEX-2T vector, and transformed into *E coli* strain DH5-α. Fusion proteins were induced in the presence of 0.5 mM IPTG and the bacterial cells harvested for further analysis according to standard protocols, for example as described in Smith et al. (1988) *Gene* 67:31-40.

In order to subclone the AG1 cDNA insert into pET-11A, oligonucleotide primers corresponding to the 5' (AG1 5'-PCR, 5'-GTCATATGGCACGAGAATTACCATCTGAT-3') (SEQ ID NO:5) and complementary to the 3'(AG1 3'-PCR, 5'-GACATATGTTAATTTCTCATTTGTACTTG-3') (SEQ ID NO:6) ends of the cDNA, containing engineered NdeI sites, were synthesized for direct DNA amplification. The amplification was carried out in the presence of Taq polymerase (Perkin Elmer Cetus, Rexdale, Ontario) in a standard 100 ml PCR reaction mixture containing 1.0 µg template, 100 mM of each primer and 0.2 mM dNTPs for 30 cycles at 94° C. (1 min), 50° C. (1 min), and 72° C. (1 min) according to the manufacturer's instructions (Perkin Elmer Cetus, Rexdale, Ontario). The amplified cDNA was digested with Nde1. The isolated insert was subcloned into the NdeI site of pET-11A and transformed in *E. coli* DH5-α. Plasmids containing inserts were electroporated into *E. coli* expression strain BL21/IDE3/plyS (Novagen, Madison, Wis.) and fusion proteins were induced in the presence of 0.5 mM IPTG and the bacterial cells harvested for protein analyses using routine protocols, for example as described in Studier et al. (1990) *Methods Enzymol.* 185:60-89.

Expression of *C. parvum* recombinant protein by the PGEX and pET vectors was evaluated by polyacrylamide gel electrophoresis and coomaissie staining followed by immunoblotting onto Immobilon-P transfer membranes using standard techniques, for example as described in Sambrook et al, supra. Immunoblots containing induced and uninduced proteins were blocked with 5% skim milk in TBST overnight at 4° C. Recombinant protein was detected using preabsorbed human immune sera prepared as described above.

The predicted size of the AG1 fusion protein with glutathione-s-transferase using the pGEX-2T vector was 43 Kd. An SDS-PAGE analysis of induced versus induced proteins produced an insoluble band as predicted at approximately 43 Kd and an additional insoluble band of lesser intensity at approximately 66 Kd. Both bands were recognized on immunoblot by human immune sera and monoclonal antibodies generated against the 43 Kd band purified by gel electrophoresis and electroelution. When AG1 was expressed in the pET 11A vector, an insoluble band of the predicted size of about 20 Kd was produced and was recognized by human immune sera and monoclonal antibody.

The predicted size of the AG2 fusion protein with glutathione-S-transferase using pGEX-2T vector was approximately 46 Kd. An SDS-PAGE analysis of induced versus uninduced protein failed to produce a recombinant fusion protein band at the expected molecular weight but produced an easily visualized insoluble band at 98 Kd. Immunoblot analysis with human immune serum and with monoclonal antibody generated against the purified 98 Kd band revealed the presence of a weak band at approximately 44 Kd and an intense band at 98 Kd. These bands did not appear in the uninduced control lanes. Sequencing of the expression vector confirmed the size of the predicted open reading frame.

Example 3

Production and Purification of Antibodies from Human Serum

Recombinant cryptosporidial proteins expressed as GST fusion proteins were purified by preparative gel electrophoresis and electroelution and used to immunize BalbC mice. Mice were immunized intraperitoneally three times at four week intervals with 50 mg of purified recombinant antigen in RIBI™ adjuvant (RIBI ImmunoChem Research Inc., Hamilton, Mont.). A final boost of 50 mg of purified recombinant antigen in phosphate buffered saline was given by intravenous injection. Three days later the animals were sacrificed and the spleens harvested. Splenocytes were fused with NS-1 using PEG (Gibco) and cultured in 96 well plates as described in Studier et al, supra. Positive hybridomas were selected by enzyme immunoassay (EIA) in which wells were coated with purified recombinant antigen expressed in the pET 11A vector (AG1), or doubly screened with purified recombinant GST fusion protein and GST (AG2) to identify cryptosporidial specific hybridomas according to standard protocols, e.g., Wilkins et al. (1996) *J. Biol. Chem.* 271:3046-3051.

Purified recombinant cryptosporidial antigens were resolved by electrophoresis, transferred to Immobilon-P membranes, and immunoblotted with human immune sera diluted 1:200 in PBS. Antibodies were acid eluted as previously described (see, e.g., Peterson et al., (1990) *Infect. Immun.* 60:2343-2348), concentrated by centrifugation in a Centricon-10 apparatus (Amicon Inc., Beverly, Mass.) to a final volume of 0.5 ml in PBS according to the manufacturer's instructions, and used to immunoblot cryptosporidial proteins as described above.

A total of 12 individual monoclonal antibodies were isolated which reacted with the AG1 PETII purified recombinant fusion protein specifically in an EIA. Four monoclonal antibodies were identified which reacted specifically with the cryptosporidial fusion portion of the AG2 GST fusion protein. Two monoclonal antibodies, 1101 directed against Ag1 and 222 directed against AG2, were selected for further study based on their reactivity by Immunoblot with native proteins and EIA against recombinant protein.

The immunoblots of affinity purified human antibodies and monoclonal antibody 1101 (AG1) directed against soluble and insoluble cryptosporidial proteins are presented in FIGS. 3A and 3B, respectively. Human antibodies eluted from the AG1 GST fusion protein recognized a faint band in total cryptosporidial protein at approximately 22 Kd (FIG. 3A), while monoclonal antibody 1101 generated against the AG1 GST fusion protein recognized a faint 22 Kd band in insoluble cryptosporidial protein (FIG. 3B lane 1) and three bands at approximately 22, 32, and 96 Kd in soluble cryptosporidial protein (FIG. 3B lane 2).

The immunoblots of affinity purified human antibodies and monoclonal antibody 222 (AG2) directed against soluble and insoluble cryptosporidial proteins are presented in FIGS. 4A and 4B, respectively. Human antibodies eluted from the AG2 GST fusion protein recognized three bands in total cryptosporidial protein at approximately 17, 34, and 84 Kd (FIG. 4A) while monoclonal antibody 222 generated against the AG2 GST fusion protein recognized no bands in insoluble cryptosporidial protein (FIG. 4B lane 1) and five bands at approximately 6, 10, 22, 34 and 84 Kd in soluble cryptosporidial protein (FIG. 4B lane 2). The intense band at 55 Kd in FIG. 4B lanes 1 and 2 was artifactual.

Example 4

In Situ Localization

Previously purified oocysts were washed three times in PBS and resuspended at a density of $5 \times 10^7$ oocysts/ml and either used directly or excysted to generate sporozoites as previously described in Example 5A. Sporozoites were quantitated by hemocytometry prior to use. Approximately $0.5 \times 10^6$ oocysts or sporozoites were aliquoted onto slides and allowed to air dry at 37° C. Slides were fixed for 10 min in 100% methanol, dried, and washed three times in PBS. Slides were blocked in 1% BSA/0.1% sodium azide in PBS for 1 hr. at 40° C., washed 3× in PBS and incubated with primary monoclonal antibody at 5 mg/ml in PBS/1% BSA/0.1% sodium azide for 1 hr at 40° C. After washing 3× in PBS, 1:100 dilution of secondary antibody (1.4 mg/ml—Rhodamine goat anti-mouse antisera (Jackson Immunoresearch Laboratories, West Grove, Pa.) in the same buffer was added and incubated for 1 hr in the dark at 40° C. The slides were washed 3× in PBS and fluorescence was detected microscopically (Olympus BH5 Model BH2 PM-10ADS) and documented photographically (Kodak Provia 1600).

The results of immunolocalization of monoclonal antibodies 1101 (AG1) and 222 (AG2) against oocysts and sporozoites are presented in FIGS. 5A, B, C and 5D, E and F, respectively. Monoclonal antibody JB1 directed against human integrin non specifically labelled debris in the slide (FIG. 5A). Monoclonal antibody 1101 directed against AG1 intensely stained in a diffuse pattern single and pairs of oocysts (FIG. 5B). Monoclonal antibody 222 directed against AG2 stained single oocysts and clumps with a ring-like pattern (FIG. 5C). Sporozoites were not visualizable with monoclonal antibody JB1 (FIG. 5D). Monoclonal antibody 1101 detected sporozoites with an even staining pattern (FIG. 5E), while monoclonal antibody 222 detected sporozoites with an intense pattern (FIG. 5F).

Example 5

Neutralizing Effect of Monoclonal Antibodies

A. Purification of C. parvum Sporozoites

Oocysts were suspended at $5.0 \times 10^7$/ml in Hank's balanced salt solution and incubated at 37° C. for 1.5 hours to release sporozoites. Sporozoites were purified on a DEAE-cellulose column equilibrated at 4° C. overnight in column buffer (80 mM $Na_2HPO_4$, 58 mM NaCl, 55 mM glucose). Excysted sporozoites were washed twice in column buffer, pelleted at 3500×G, and resuspended in 20 ml of column buffer. The pelleted sporozoites were applied to one cm of matrix suspended in a Econo-column (BioRad). 50 ml of column buffer were used to elute the sporozoites which were pelleted and washed twice with Hank's Balanced salt solution. Sporozoites were quantitated by hemocytometry and the concentration adjusted to yield a final concentration of $0.5 \times 10^6$/ml.

B. In Vitro Invasion Assay

HT-29 cells were obtained from the American Tissue Culture Collection. Cells were originally cultured in Dulbecco's Modified Eagle Medium (DMEM) plus glutamine (Gibco-BRL) supplemented with 10% fetal calf serum (Intergen) in a 5% $CO_2$ atmosphere. Prior to use in the in vitro invasion assay, cells were transitioned from DMEM to Leibovitz's L-15 medium (Gibco-BRL), 10% fetal calf serum and 5 μg/ml penicillin/streptomycin (Gibco-BRL)) in a 5% $CO_2$ atmosphere and passaged 30 times to permit differentiation in the glucose free medium as previously described, for example in Flanigan et al. (1991) Infect. Immun. 59:234-239.

Three monoclonal antibodies were used in these experiments. Monoclonal antibody 1101 is an IgG directed against cryptosporidial antigen 1 (AG1) and monoclonal antibody 222 is an IgG directed against cryptosporidial antigen 2 (AG2). As described above, both monoclonal antibodies detect native protein on immunoblot, react with recombinant protein in EIA, and localize to oocysts and sporozoites in immunofluorescence studies. Monoclonal antibody 2F12 is a negative control IgG antibody directed against the lipooligosaccharide surface of the bacterium Hemophilus ducreyi (provided by Dr. Ian McClean). For the assay, cells were grown on cover slips to approximately 80% confluency and exposed to $5 \times 10^5$ sporozoites in addition to titrating doses of monoclonal antibodies as follows: monoclonal antibodies 1101, 222 and 2F12 at concentrations of 0, 1, 2, 4, 8, 10, 20, 40, 80 μg/ml of culture medium. To determine if neutralization effects were additive or synergistic antibodies were added in combination at a final concentration of 4 μg/ml of each monoclonal antibody as follows: 1101, 222, 2F12; 1101+222; 2F12+222; 2F12+1101.

Exposed cells were cultured for 48-72 hours, fixed in 100% methanol, and stained for evaluation by Hematoxylin and Eosin as previously described, for example in Cotran et al. "Pathological Basis of Disease" (1998), W.B. Saunders Co. Each experiment was performed in triplicate and the number of infected cells per 25 fields on each slide determined by light microscopy. Differences were determined to be significant using T-testing in the Statistical Package for Social Sciences (SPSS) statistical program, available, for example, on the World Wide Web.

The effect of increasing concentrations of monoclonal antibodies 1101 and 222 compared to control monoclonal antibody 2F12 on sporozoite invasion of HT-29 cells is presented in Table 1 and graphically in FIG. 6.

TABLE 1

Comparison of neutralization activity of monoclonals 1101 and 222 versus 2F12 in a HT-29 invasion assay.

| | Mab | Mean ± SD Infected cells 25 Fields | P value |
|---|---|---|---|
| 0 ug/ml | 2F12 | 29.3 ± 2.5 | |
| | 1101 | 29.3 ± 2.5 | ns |
| | 222 | 23.0 ± 3.6 | ns |
| 1 ug/ml | 2F12 | 30.0 ± 4.6 | |
| | 1101 | 24.7 ± 3.5 | ns |
| | 222 | 4.3 ± 0.6 | 0.001 |

TABLE 1-continued

Comparison of neutralization activity of monoclonals 1101 and 222 versus 2F12 in a HT-29 invasion assay.

| | Mab | Mean ± SD Infected cells 25 Fields | P value |
|---|---|---|---|
| 2 ug/ml | 2F12 | 30.0 ± 6.0 | |
| | 1101 | 13.3 ± 2.9 | 0.012 |
| | 222 | 5.7 ± 3.1 | 0.003 |
| 4 ug/ml | 2F12 | 29.7 ± 2.9 | |
| | 1101 | 8.0 ± 1.0 | 0.003 |
| | 222 | 4.7 ± 1.5 | 0.000 |
| 8 ug/ml | 2F12 | 28.7 ± 3.5 | |
| | 1101 | 11.0 ± 3.0 | 0.003 |
| | 222 | 5.0 ± 3.0 | 0.001 |
| 10 ug/ml | 2F12 | 26.7 ± 7.5 | |
| | 1101 | 13.0 ± 6.1 | 0.070 |
| | 222 | 8.0 ± 2.0 | 0.014 |
| 20 ug/ml | 2F12 | 25.3 ± 2.5 | |
| | 1101 | 8.7 ± 2.5 | 0.001 |
| | 222 | 7.3 ± 1.5 | 0.000 |
| 40 ug/ml | 2F12 | 27.3 ± 4.5 | |
| | 1101 | 11.3 ± 4.1 | 0.011 |
| | 222 | 4.7 ± 1.5 | 0.001 |
| 80 ug/ml | 2F12 | 26.3 ± 6.8 | |
| | 1101 | 15.3 ± 4.5 | 0.080 |
| | 222 | 5.3 ± 0.6 | 0.006 |

The reduction in infectivity for AG1 monoclonal antibody 1101 became significant at 2 ug/ml although at 10 and 80 μg/ml statistical significance was not achieved. Over all the range of concentrations tested, monoclonal antibody 1101 resulted in a 53% reduction of infectivity which was highly significant (p<0.001). Monoclonal antibody 222 directed against AG2 had a more dramatic and sustained neutralizing activity when compared to monoclonal 1101. Over the range 1-80 μg/ml neutralization was observed. The mean reduction in infectivity resulting from the presence of monoclonal 222 was 80% which was highly significant (p<0.0001).

To determine if the neutralizing effects of the monoclonal antibodies were additive, synergistic, or competitive, combinations were assayed maintaining the concentration of each added monoclonal antibody at 4 μg/ml, a level at which differences were consistently significant. The results of these studies are presented graphically in FIG. 7.

The addition of monoclonal antibodies 1101 and 222 to the cultures had no additive or synergistic effect on reduction in infectivity when compared to either alone or in combination with the non specific antibody 2F12. Although the reductions in infectivity were significant when compared to the negative control (p<0.001) and the non specific antibody 2F12 (p<0.002), there was no discernable interaction between any of the antibody combinations on infectivity. In no instance did neutralization reach 100%. This suggests that the mechanism of infectivity is saturable for this pathway and perhaps ancillary pathways may be used to achieve invasion. It is also possible that the antibodies did not completely block invasion although blocking two different antigens might be predicted to have an additive effect unless the two antibodies competed for a similar site in the invasion process.

Thus, the cloning, expression and characterization of *C. parvum* antigenic polypeptides and antibodies which recognize epitopes on these polypeptides are disclosed, as are methods of using the same. Although preferred embodiments of the subject invention have been described in some detail, it is understood that obvious variations can be made without departing from the spirit and the scope of the invention as defined by the appended claims.

A deposit of hybridomas useful in practicing the invention was made with the American Type Culture Collection, 10801 University Boulevard, Manassas, Va. (deposits received by ATCC May 16, 2000, ATCC Patent Deposit Designations PTA-1879 and PTA-1880).

The invention claimed is:

1. A composition comprising a pharmaceutically acceptable vehicle and an immunogenic *C. parvum* polypeptide comprising the amino acid sequence of SEQ ID NO:4, or a polypeptide with at least 90% sequence identity to a polypeptide comprising the amino acid sequence of SEQ ID NO:4.

2. The composition of claim 1, wherein said immunogenic polypeptide comprises an amino acid sequence having at least 90% sequence identity to the amino acid sequence of SEQ ID NO:4.

3. The composition of claim 1, wherein said immunogenic polypeptide comprises the amino acid sequence of SEQ ID NO:4.

4. The composition of claim 1, further comprising an adjuvant.

5. The composition of claim 2, further comprising an adjuvant.

6. The composition of claim 3, further comprising an adjuvant.

7. A method of treating *C. parvum* infection in a mammalian subject comprising administering to said subject a therapeutically effective amount of a composition according to claim 1.

8. A method of treating *C. parvum* infection in a mammalian subject comprising administering to said subject a therapeutically effective amount of a composition according to claim 2.

9. A method of treating *C. parvum* infection in a mammalian subject comprising administering to said subject a therapeutically effective amount of a composition according to claim 3.

10. A method of treating *C. parvum* infection in a mammalian subject comprising administering to said subject a therapeutically effective amount of a composition according to claim 4.

11. A method of treating *C. parvum* infection in a mammalian subject comprising administering to said subject a therapeutically effective amount of a composition according to claim 5.

12. A method of treating *C. parvum* infection in a mammalian subject comprising administering to said subject a therapeutically effective amount of a composition according to claim 6.

13. A method of producing a composition comprising:
  (a) providing an immunogenic *C. parvum* polypeptide comprising the amino acid sequence of SEQ ID NO:4, or a polypeptide with at least 90% sequence identity to a polypeptide comprising the amino acid sequence of SEQ ID NO:4, and
  (b) combining said immunogenic polypeptide with a pharmaceutically acceptable vehicle.

14. The method of claim 13, wherein said immunogenic polypeptide comprises an amino acid sequence having at least 90% sequence identity to the amino acid sequence of SEQ ID NO:4.

15. The method of claim 13, wherein said immunogenic polypeptide comprises the amino acid sequence of SEQ ID NO:4.

* * * * *